United States Patent
McGuckin, Jr. et al.

(10) Patent No.: US 7,344,518 B2
(45) Date of Patent: *Mar. 18, 2008

(54) APPARATUS FOR DELIVERING ABLATION FLUID TO TREAT LESIONS

(75) Inventors: James F. McGuckin, Jr., Radnor, PA (US); Stephan A. DeFonzo, Wayne, PA (US); Alim S. Alli, North Haven, CT (US); Peter W. J. Hinchliffe, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 623 days.

This patent is subject to a terminal disclaimer.

(21) Appl. No.: 10/836,048

(22) Filed: Apr. 30, 2004

(65) Prior Publication Data

US 2004/0204683 A1    Oct. 14, 2004

Related U.S. Application Data

(63) Continuation of application No. 10/081,695, filed on Feb. 22, 2002, now Pat. No. 6,905,480.

(60) Provisional application No. 60/348,301, filed on Nov. 7, 2001, provisional application No. 60/272,119, filed on Feb. 28, 2001.

(51) Int. Cl.
*A61M 5/178* (2006.01)
*A61M 5/32* (2006.01)
*A61B 17/34* (2006.01)

(52) U.S. Cl. .................. 604/164.01; 604/164.07; 604/272; 606/186

(58) Field of Classification Search ............... 604/158, 604/187, 164.01, 272, 164.04, 164.06, 528, 604/164.07, 264, 164.11, 65, 165.01, 173, 604/166.01; 606/198, 186, 183
See application file for complete search history.

(56) References Cited

U.S. PATENT DOCUMENTS 4,013,080 A    3/1977    Froning (Continued)

FOREIGN PATENT DOCUMENTS

CN    2389625    8/2000

(Continued)

OTHER PUBLICATIONS

T. G. Frank, W. Xu and A. Cuschieri, "Instruments based on shape-memory alloy properties for minimal access surgery, interventional radiology and flexible endoscopy", 2000 (4 pages).

(Continued)

*Primary Examiner*—Matthew F. Desanto
(74) *Attorney, Agent, or Firm*—Neil D. Gershon

(57) ABSTRACT

A surgical apparatus for delivering fluid to treat a lesion comprising an elongated member having a distal tip and a plurality of slots formed in a sidewall proximal of the distal tip, a plurality of fluid delivery members positioned in the elongated member and having a lumen and at least one opening communicating with the lumen for delivering fluid to the lesion, and an actuator actuable to a first position to move the plurality of fluid delivery members from a retracted position within the elongated member to a first deployed position extending radially with respect to the elongated member and actuable to a second position to move the plurality of fluid delivery members from the first position to a second deployed position extending further radially from the elongated member.

12 Claims, 23 Drawing Sheets

U.S. PATENT DOCUMENTS

| | | |
|---|---|---|
| RE31,873 E | 4/1985 | Howes |
| 4,645,491 A | 2/1987 | Evans |
| 4,760,847 A | 8/1988 | Vaillancourt |
| 4,808,157 A | 2/1989 | Coombs |
| 4,842,585 A | 6/1989 | Witt |
| 4,846,799 A | 7/1989 | Tanaka et al. |
| 4,869,259 A | 9/1989 | Elkins |
| 4,926,860 A | 5/1990 | Stice et al. |
| 4,958,901 A | 9/1990 | Coombs |
| 5,067,957 A | 11/1991 | Jervis |
| 5,102,396 A | 4/1992 | Bommarito |
| 5,139,485 A | 8/1992 | Smith et al. |
| 5,160,323 A | 11/1992 | Andrew |
| 5,195,526 A | 3/1993 | Michelson |
| 5,207,652 A | 5/1993 | Kay |
| 5,215,527 A | 6/1993 | Beck et al. |
| 5,231,989 A | 8/1993 | Middleman et al. |
| 5,236,424 A | 8/1993 | Imran |
| 5,242,448 A | 9/1993 | Pettine et al. |
| 5,275,611 A | 1/1994 | Behl |
| 5,354,279 A | 10/1994 | Höfling |
| 5,360,416 A | 11/1994 | Ausherman et al. |
| 5,385,148 A | 1/1995 | Lesh et al. |
| 5,385,544 A | 1/1995 | Edwards et al. |
| 5,403,311 A | 4/1995 | Abele et al. |
| 5,405,376 A | 4/1995 | Mulier et al. |
| 5,419,777 A * | 5/1995 | Hofling .................... 604/264 |
| 5,431,649 A | 7/1995 | Mulier et al. |
| 5,435,805 A | 7/1995 | Edwards et al. |
| 5,458,597 A | 10/1995 | Edwards et al. |
| 5,464,395 A | 11/1995 | Faxon et al. |
| 5,507,802 A | 4/1996 | Imran |
| 5,558,673 A | 9/1996 | Edwards et al. |
| 5,562,683 A | 10/1996 | Chan |
| 5,562,687 A | 10/1996 | Chan |
| 5,588,960 A | 12/1996 | Edwards et al. |
| 5,599,345 A | 2/1997 | Edwards et al. |
| 5,601,572 A | 2/1997 | Middleman et al. |
| 5,607,389 A | 3/1997 | Edwards et al. |
| 5,611,778 A | 3/1997 | Brinon |
| 5,620,419 A * | 4/1997 | Lui et al. .................... 604/116 |
| 5,672,174 A | 9/1997 | Gough et al. |
| 5,683,384 A | 11/1997 | Gough et al. |
| 5,693,029 A | 12/1997 | Leonhardt |
| 5,713,853 A | 2/1998 | Clark et al. |
| 5,738,650 A | 4/1998 | Gregg |
| 5,795,318 A | 8/1998 | Wang et al. |
| 5,810,804 A | 9/1998 | Gough et al. |
| 5,827,276 A | 10/1998 | LeVeen et al. |
| 5,849,011 A | 12/1998 | Jones et al. |
| 5,855,576 A | 1/1999 | LeVeen et al. |
| 5,863,290 A | 1/1999 | Gough et al. |
| 5,873,865 A | 2/1999 | Horzewski et al. |
| 5,897,531 A | 4/1999 | Amirana |
| 5,964,796 A | 10/1999 | Imran |
| 5,980,517 A | 11/1999 | Gough |
| 6,004,295 A | 12/1999 | Langer et al. |
| 6,009,877 A | 1/2000 | Edwards |
| 6,059,780 A | 5/2000 | Gough et al. |
| 6,074,367 A | 6/2000 | Hubbell |
| 6,080,150 A | 6/2000 | Gough |
| 6,102,887 A | 8/2000 | Altman |
| 6,106,521 A | 8/2000 | Blewett et al. |
| 6,129,726 A | 10/2000 | Edwards et al. |
| 6,132,425 A | 10/2000 | Gough |
| 6,159,196 A | 12/2000 | Ruiz |
| 6,179,813 B1 | 1/2001 | Ballow et al. |
| 6,190,353 B1 | 2/2001 | Makower et al. |
| 6,190,360 B1 | 2/2001 | Iancea et al. |
| 6,200,274 B1 | 3/2001 | McNeirney |
| 6,203,524 B1 | 3/2001 | Burney et al. |
| 6,217,554 B1 | 4/2001 | Green |
| 6,217,559 B1 | 4/2001 | Foster |
| 6,221,049 B1 | 4/2001 | Selmon et al. |
| 6,228,049 B1 | 5/2001 | Schroeder et al. |
| 6,231,591 B1 | 5/2001 | Desai |
| 6,254,573 B1 | 7/2001 | Haim et al. |
| 6,280,424 B1 | 8/2001 | Chang et al. |
| 6,283,951 B1 * | 9/2001 | Flaherty et al. ............. 604/529 |
| 6,302,870 B1 | 10/2001 | Jacobsen et al. |
| 6,306,141 B1 | 10/2001 | Jervis |
| 6,319,230 B1 | 11/2001 | Palasis et al. |
| 6,346,095 B1 | 2/2002 | Gross et al. |
| 6,425,887 B1 | 7/2002 | McGuckin et al. |
| 6,428,517 B1 | 8/2002 | Hochman et al. |
| 6,432,092 B2 | 8/2002 | Miller |
| 6,511,458 B2 | 1/2003 | Milo et al. |
| 6,730,061 B1 | 5/2004 | Cuschieri et al. |
| 6,905,480 B2 * | 6/2005 | McGuckin et al. .... 604/164.01 |
| 6,989,004 B2 * | 1/2006 | Hinchliffe et al. ..... 604/164.01 |
| 7,087,040 B2 * | 8/2006 | McGuckin et al. ......... 604/158 |

FOREIGN PATENT DOCUMENTS

| | | |
|---|---|---|
| WO | WO 9846119 | 10/1998 |

OTHER PUBLICATIONS

Second Department of Internal Medicine, Faculty of Medicine, University of Tokyo, Japan, Gastroenterologia Japonica (JAPAN) Feb. 1991, p. 47-50, "Multiple-needle insertion method in percutaneous ethanol injection therapy for liver neoplasms", Shiina S; Hata Y; Niwa Y; Komatsu Y; Tanaka T; Yoshiura K; Hamada E; Ohshima M; Mutoh H; Kurita M; et al.

* cited by examiner

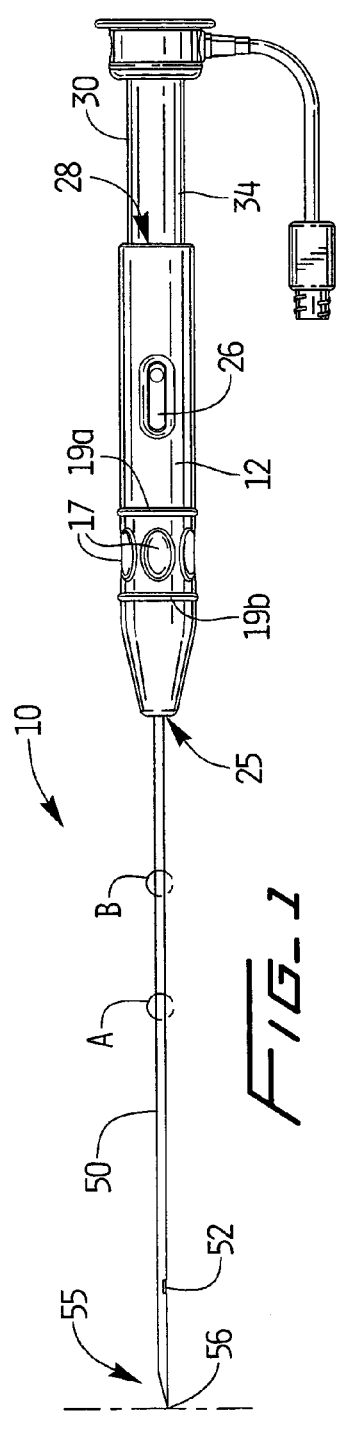
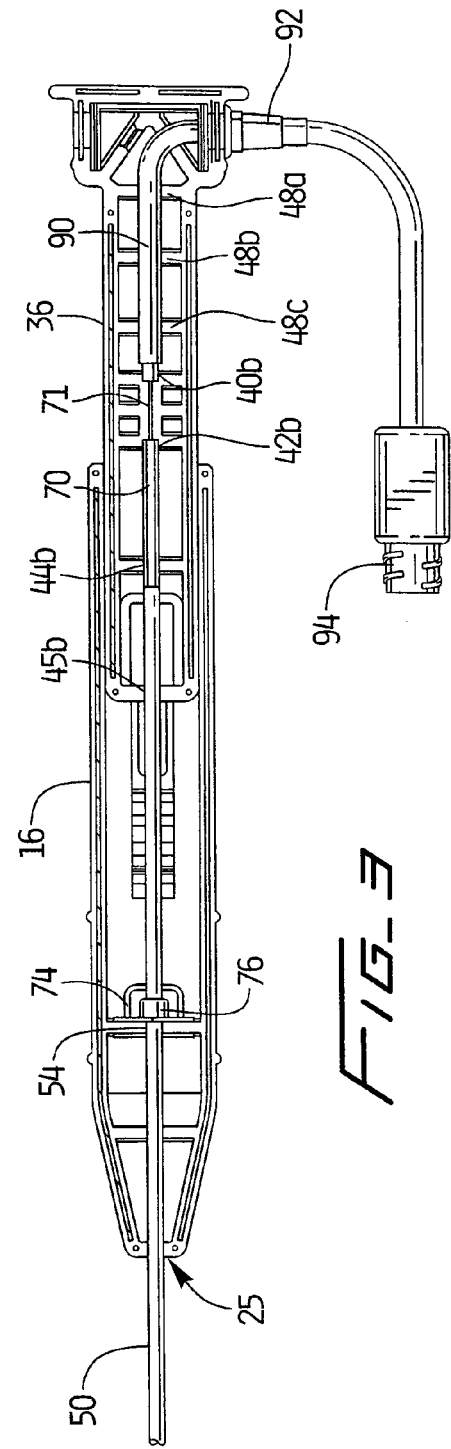

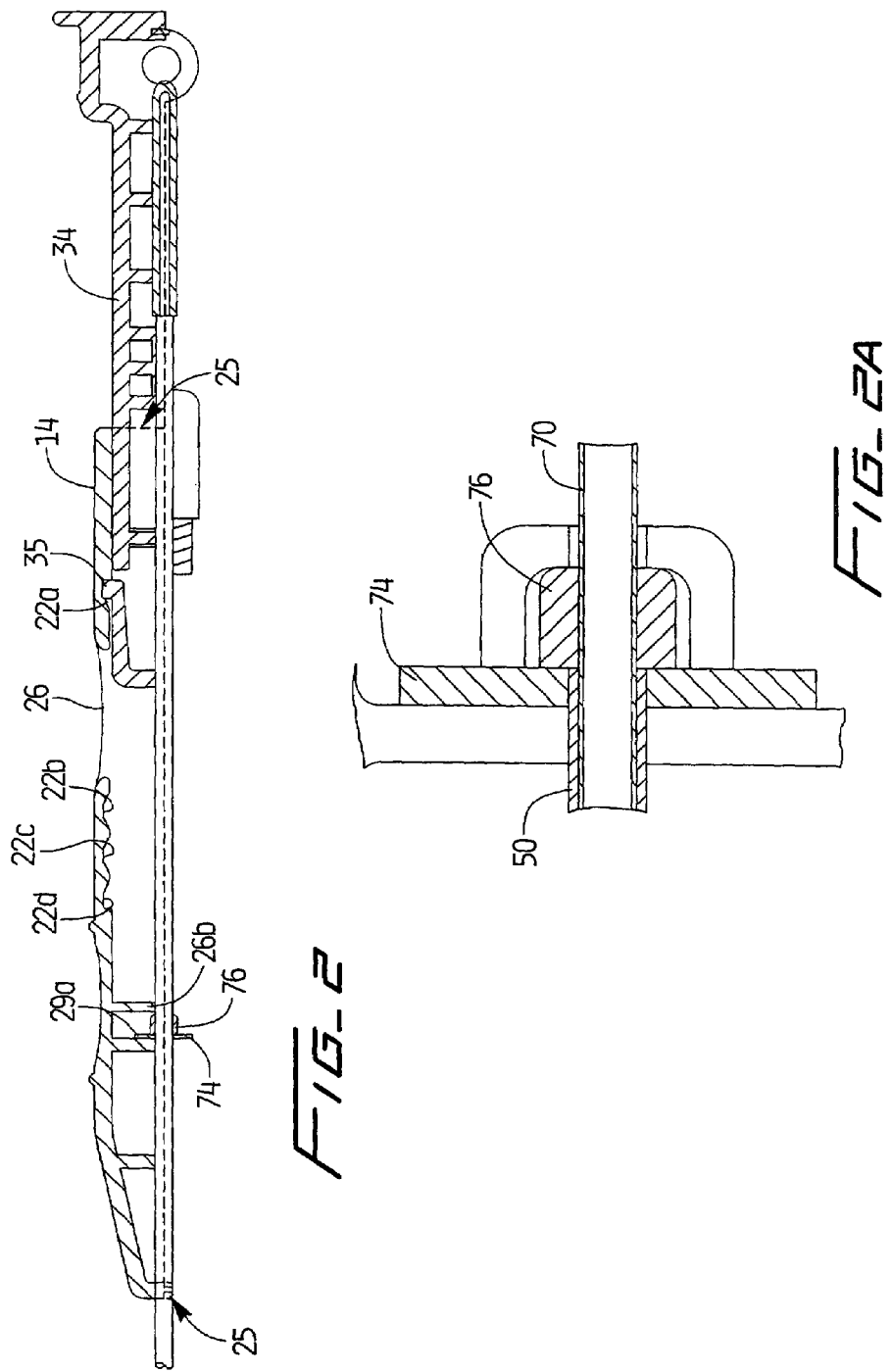

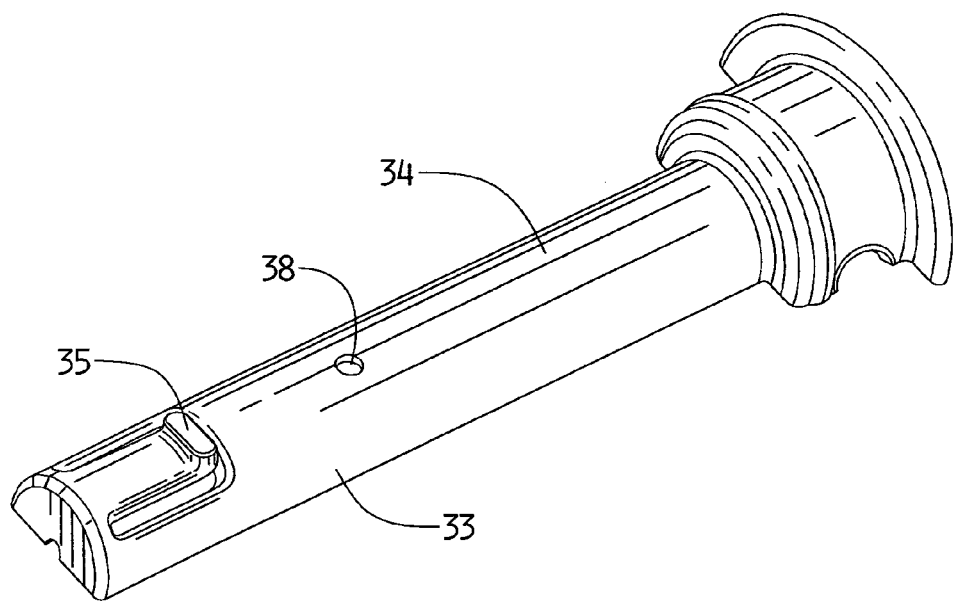
FIG_4
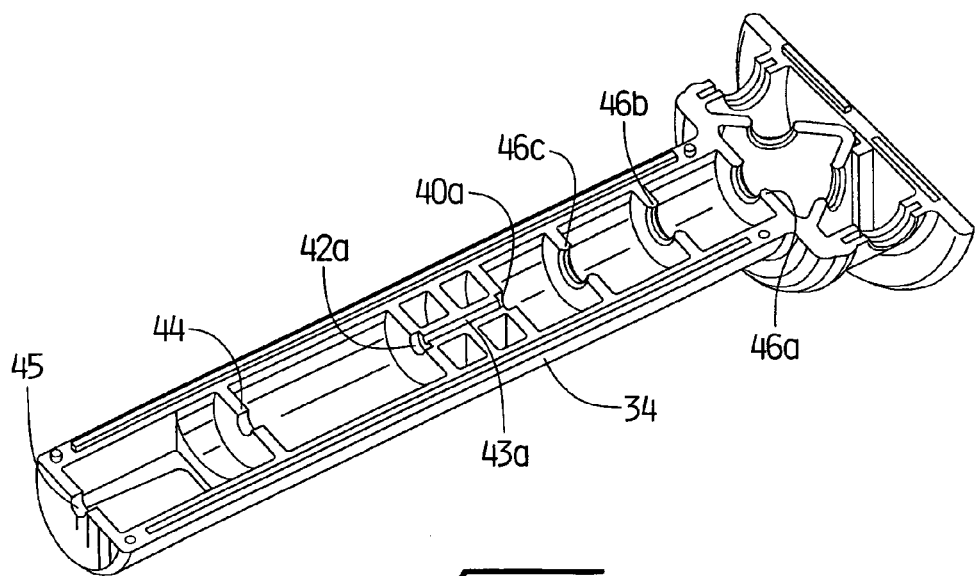
FIG_5

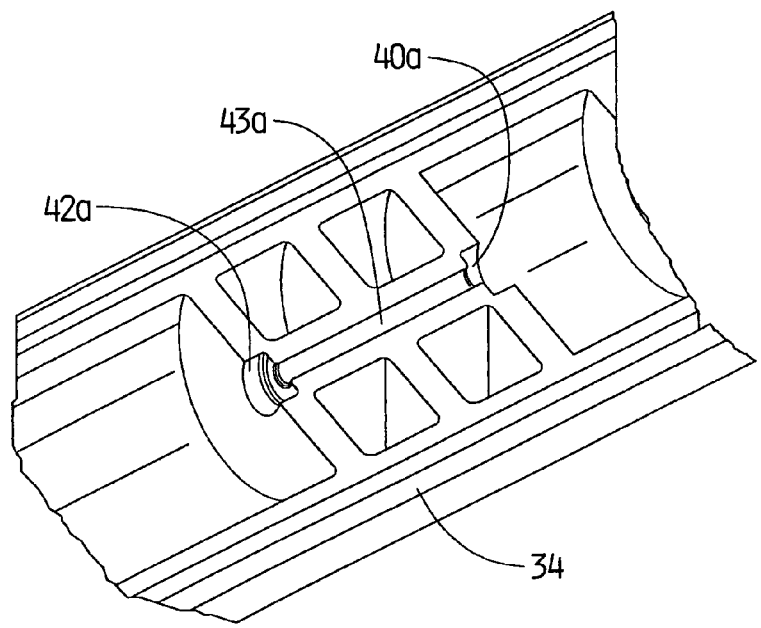
FIG_6A
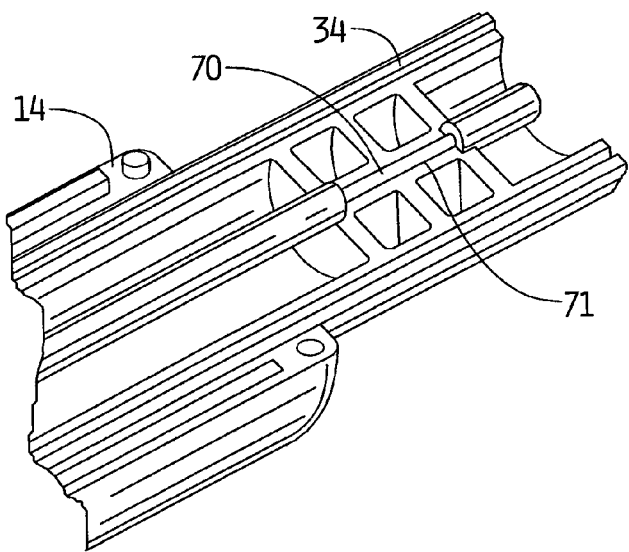
FIG_6B

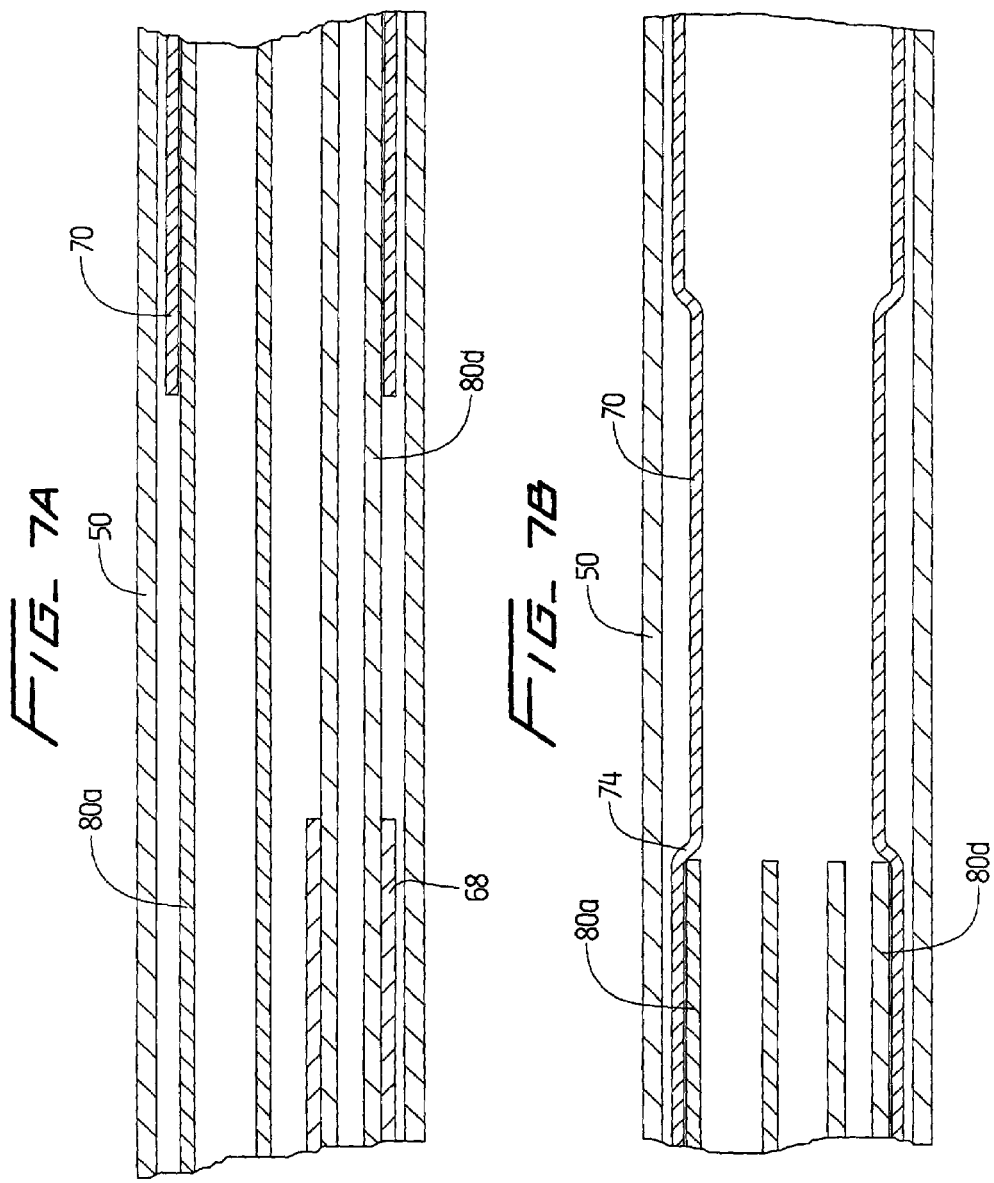

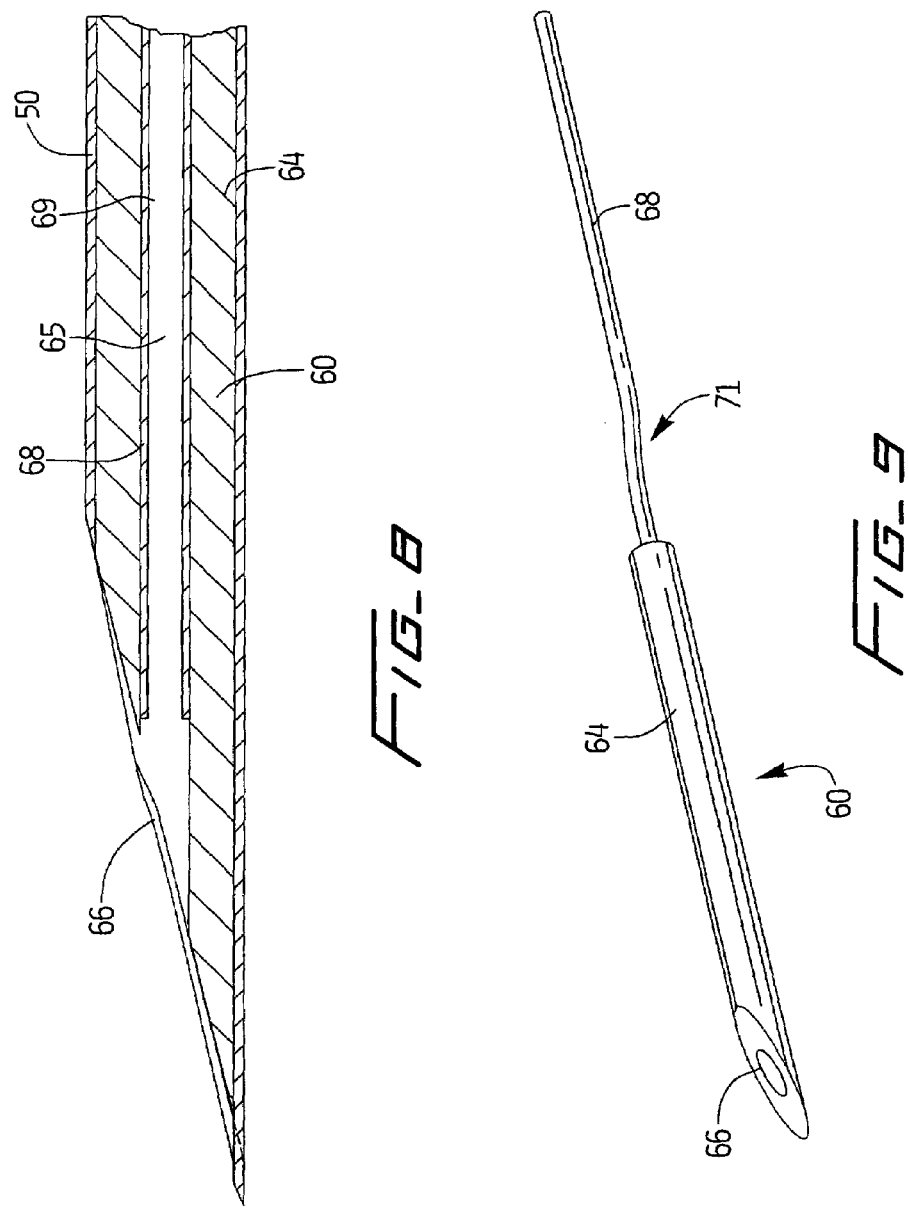

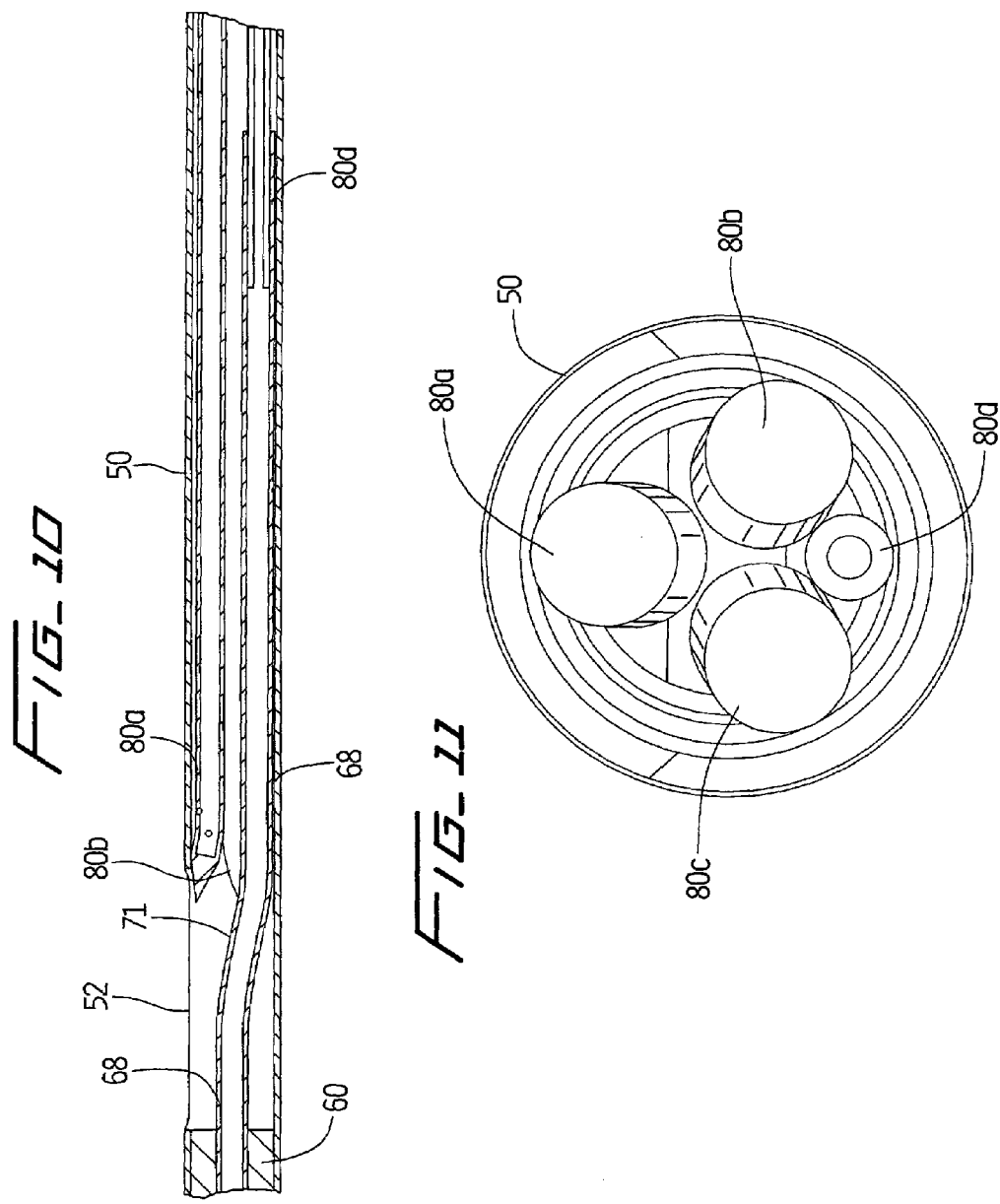

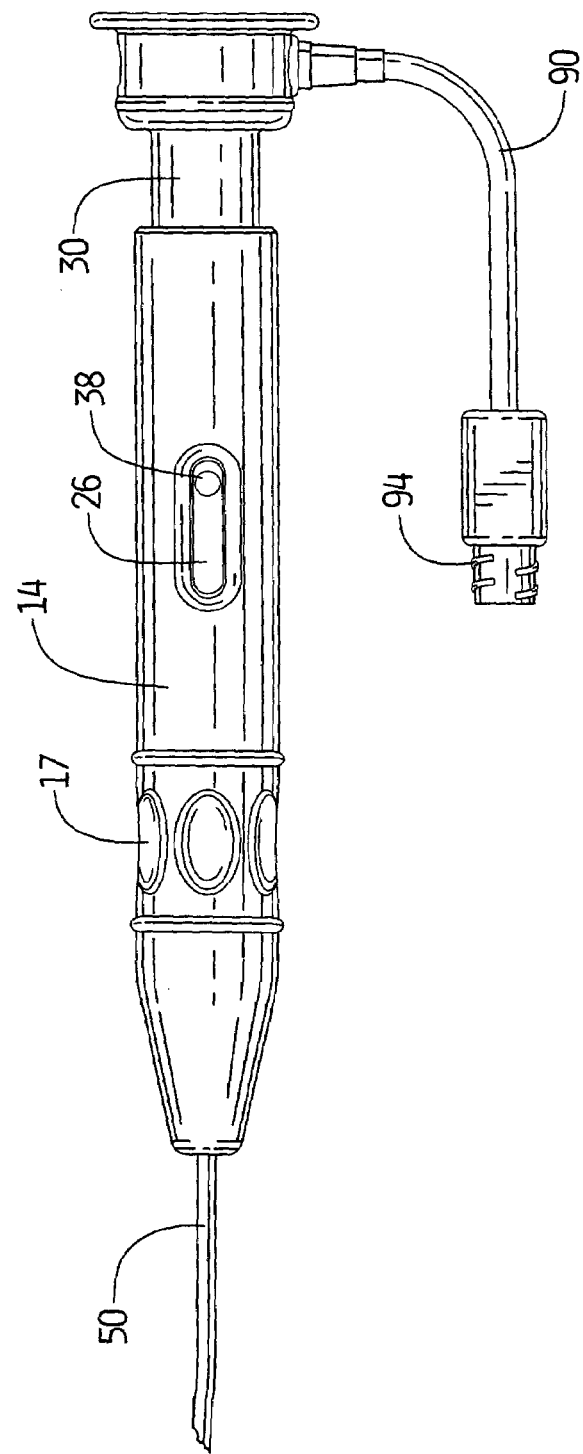

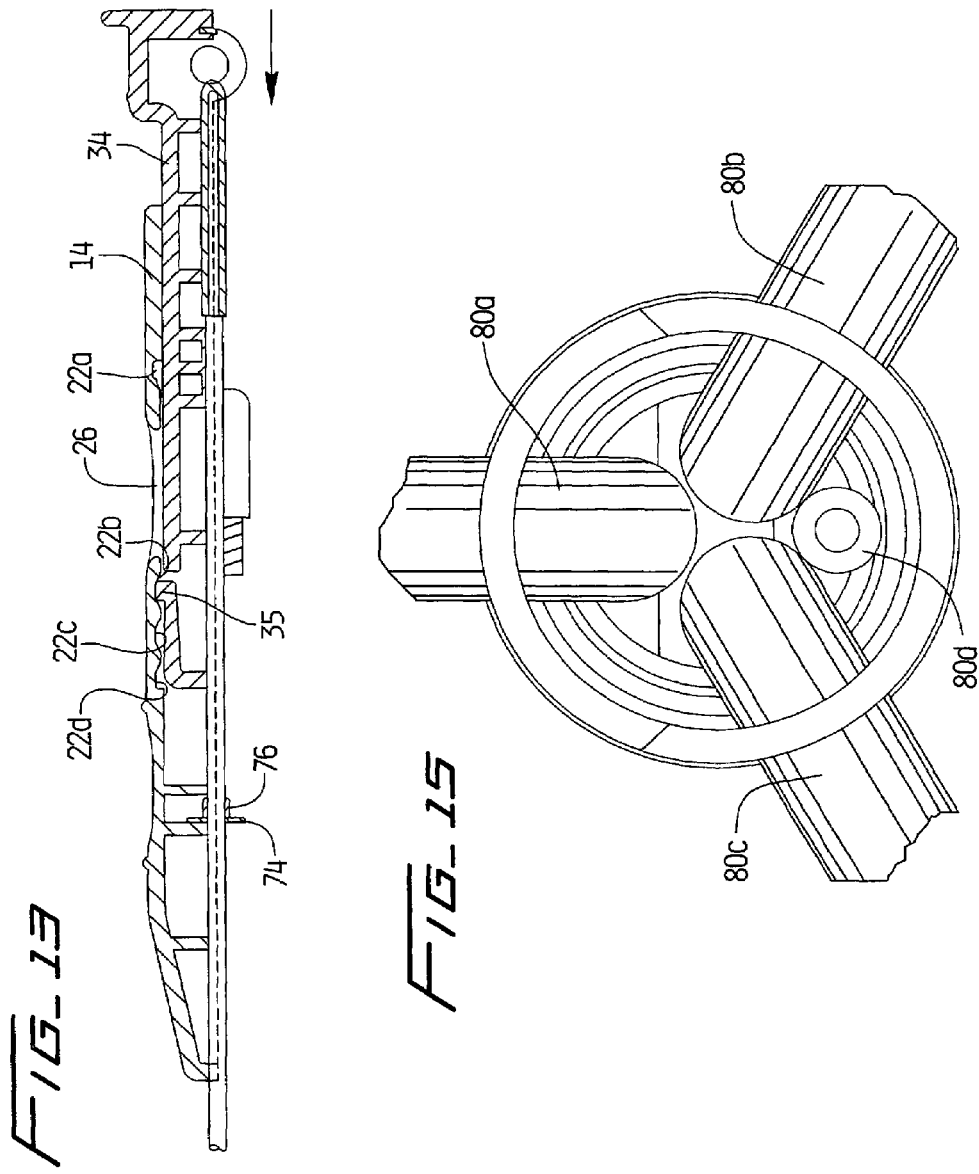

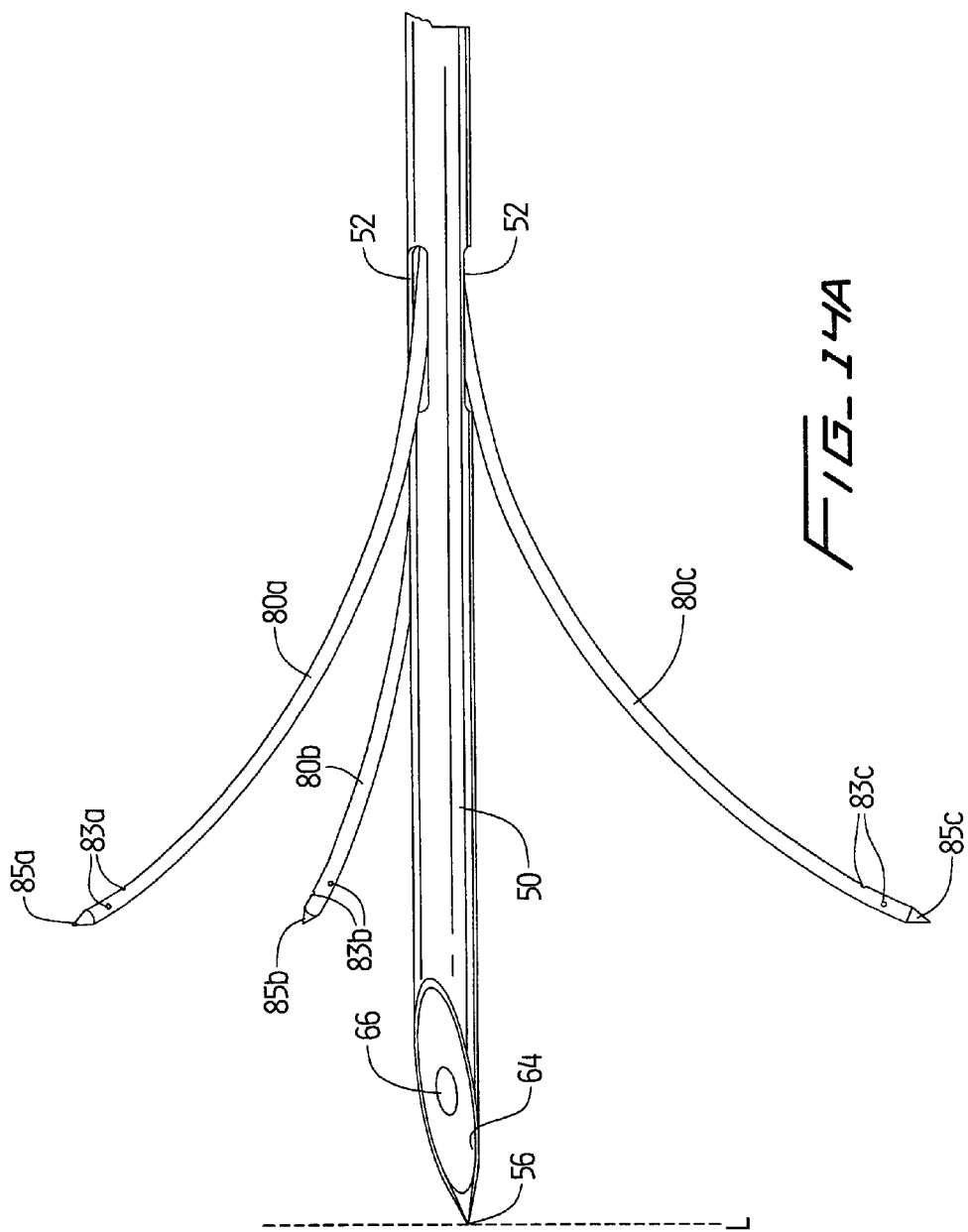

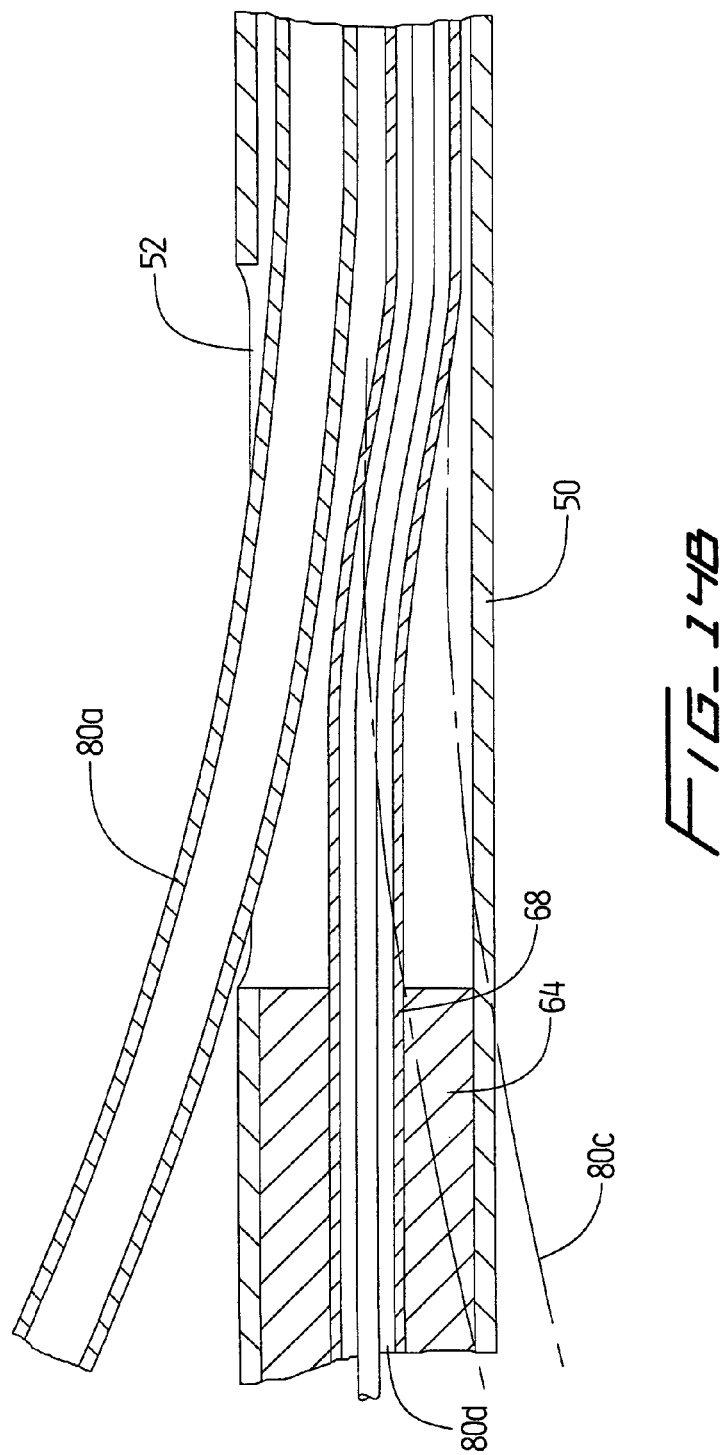
FIG_14B

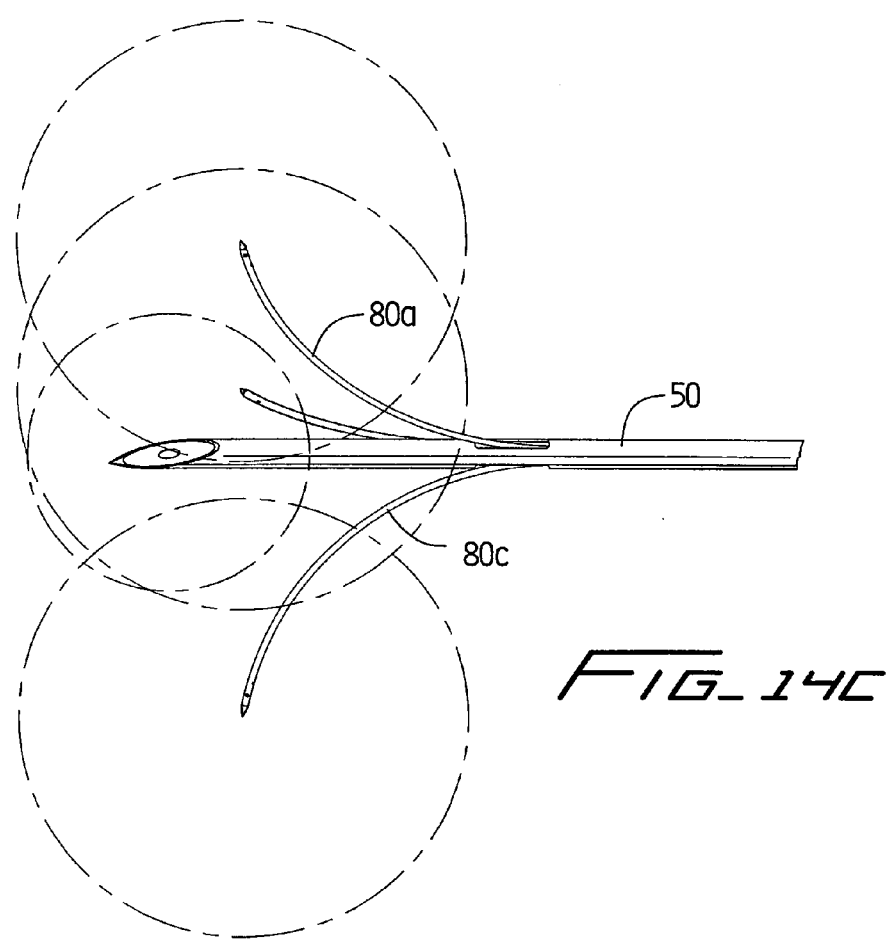
FIG_14C

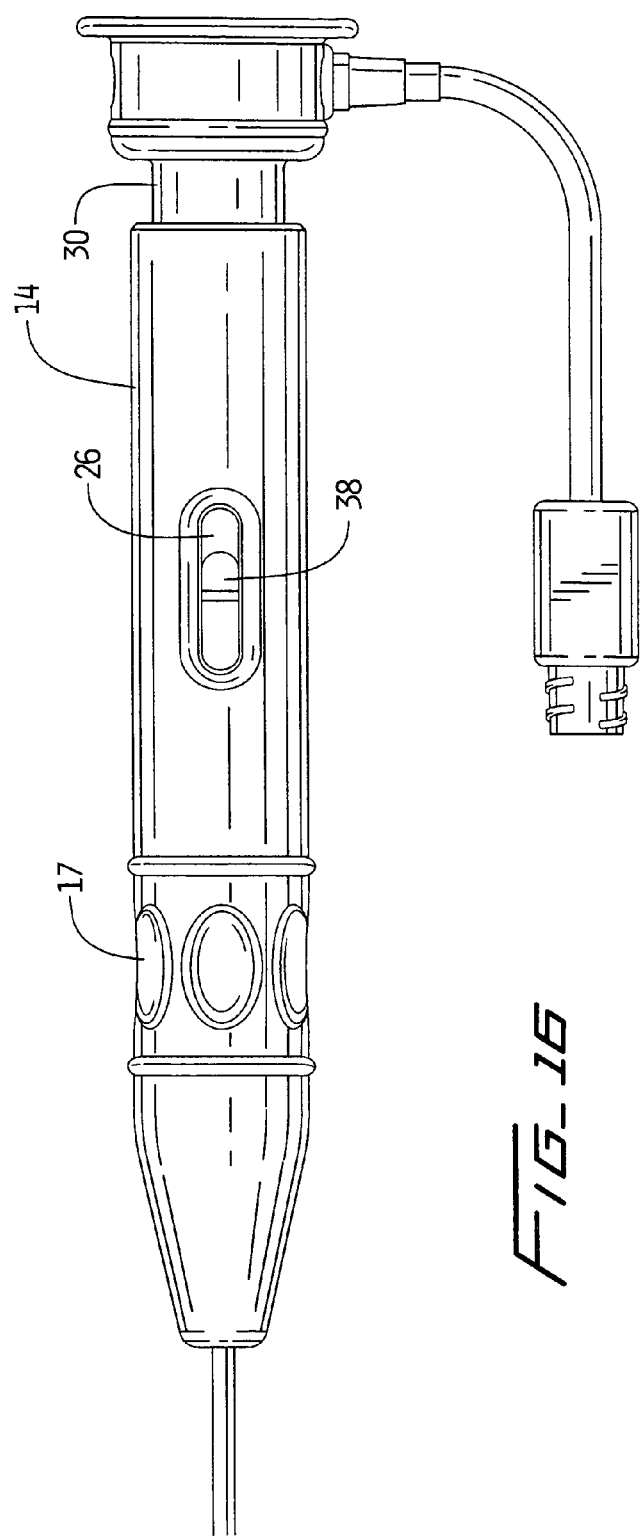

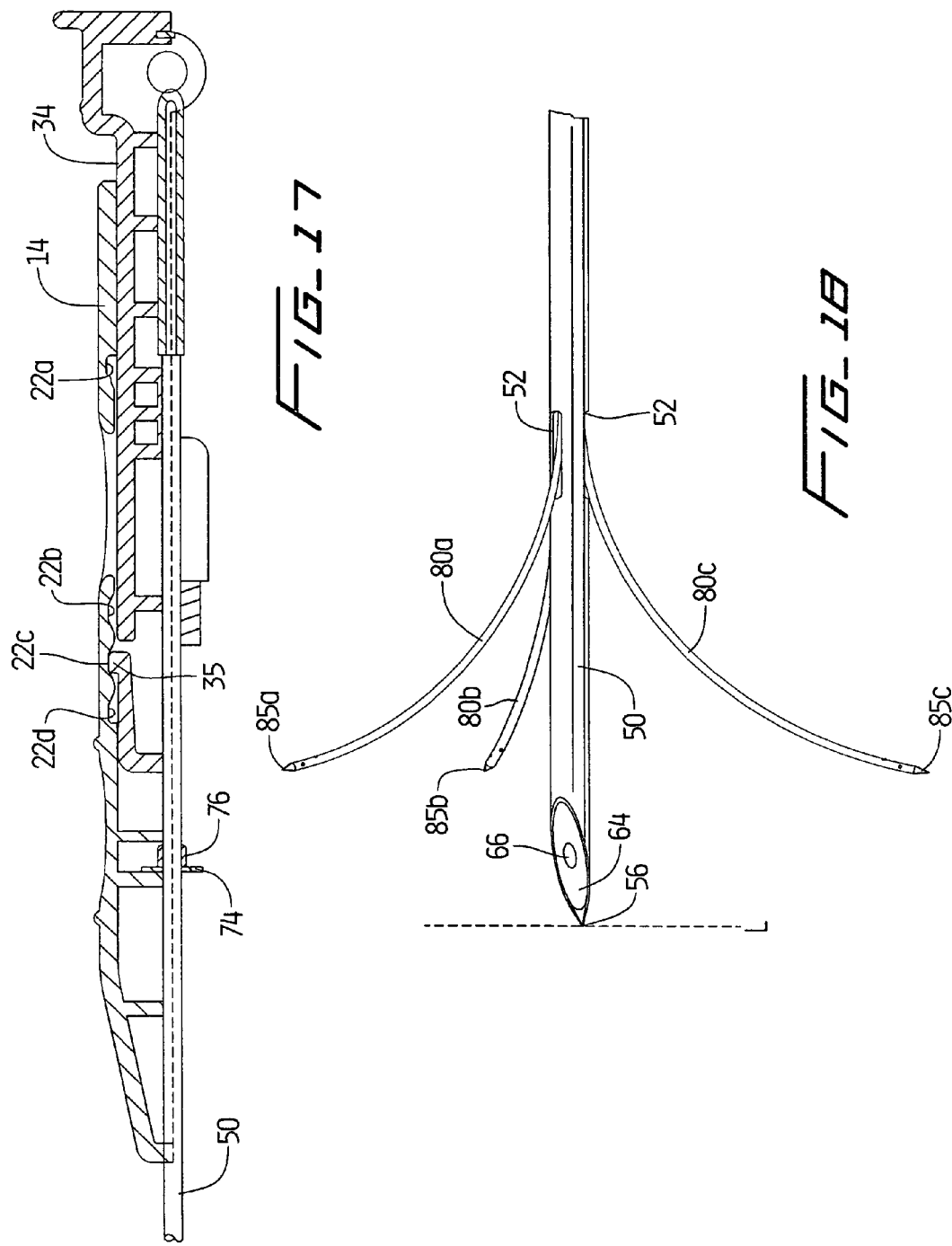

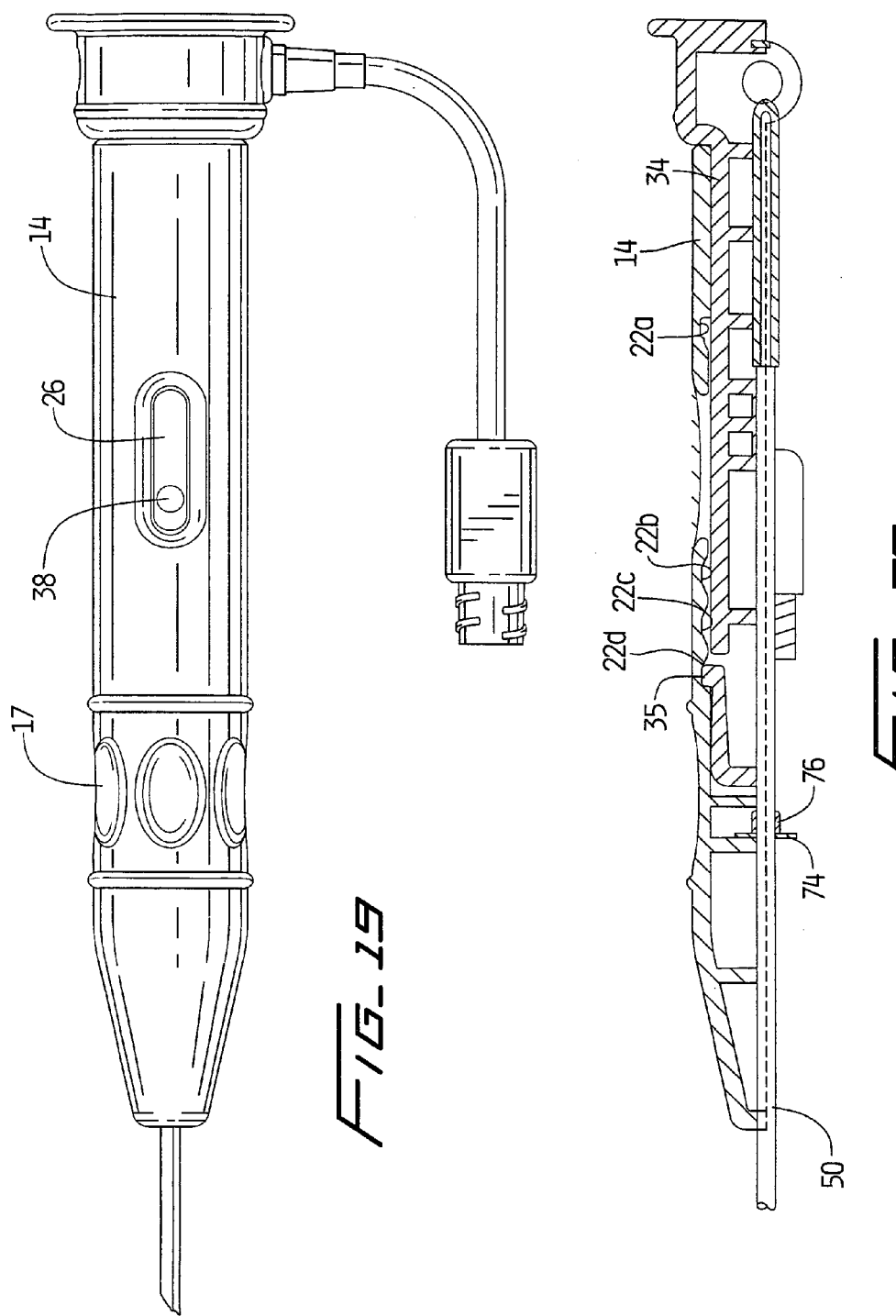

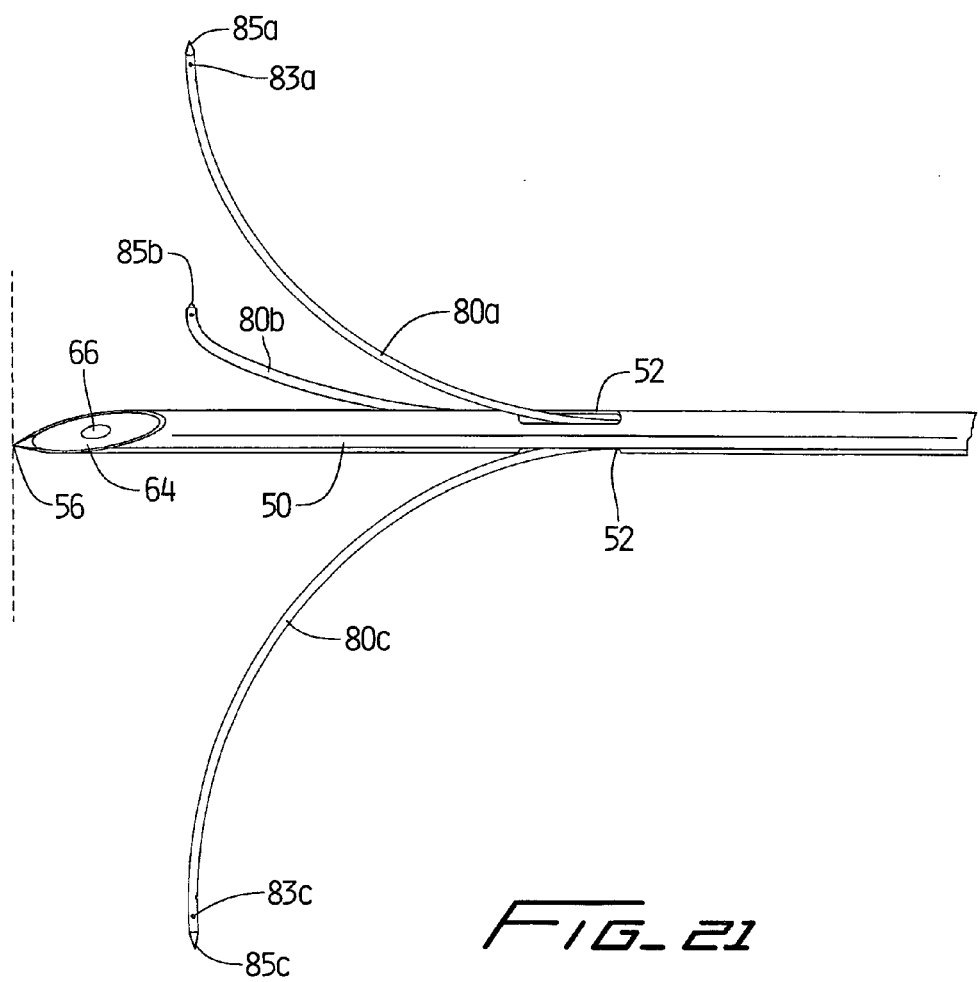
FIG_21

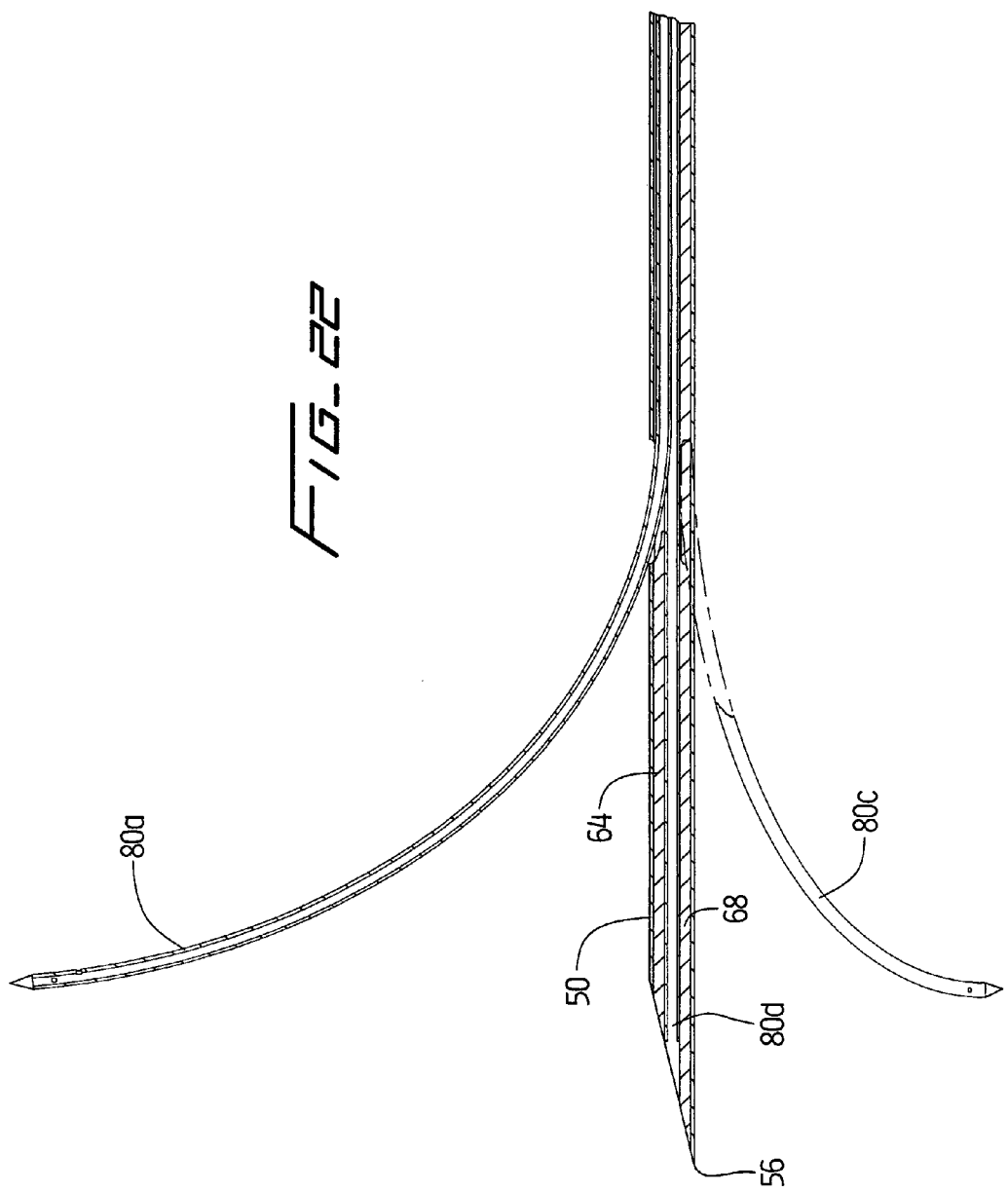

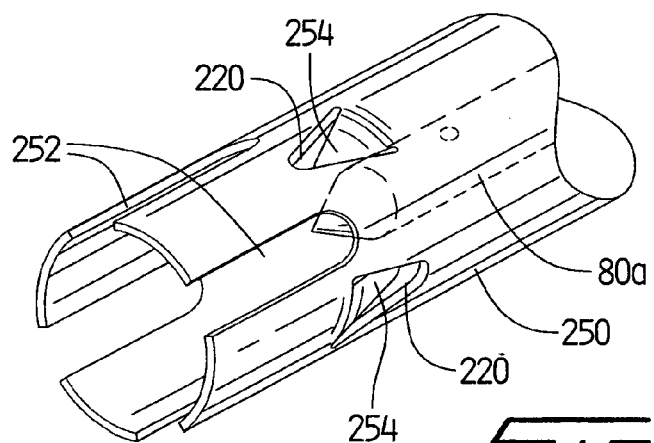
FIG_23
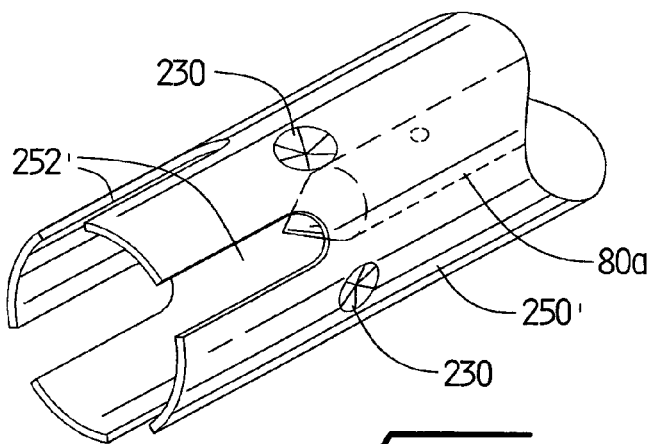
FIG_24
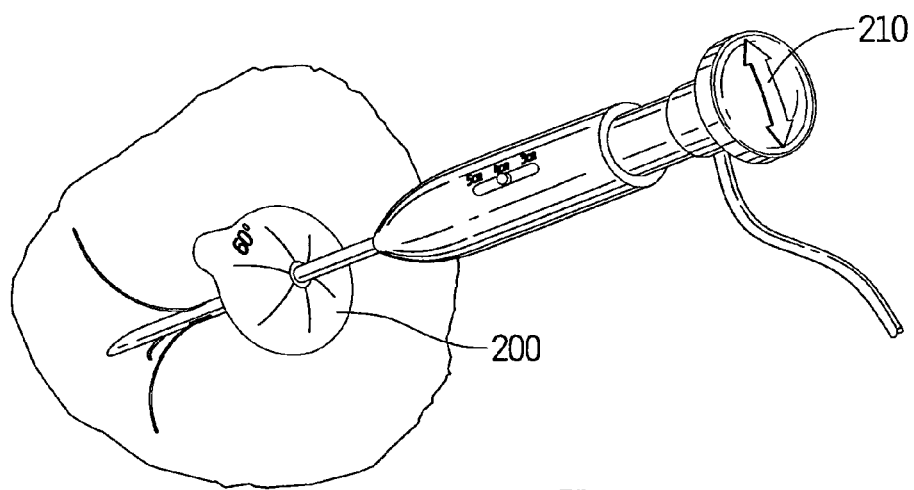
FIG_25

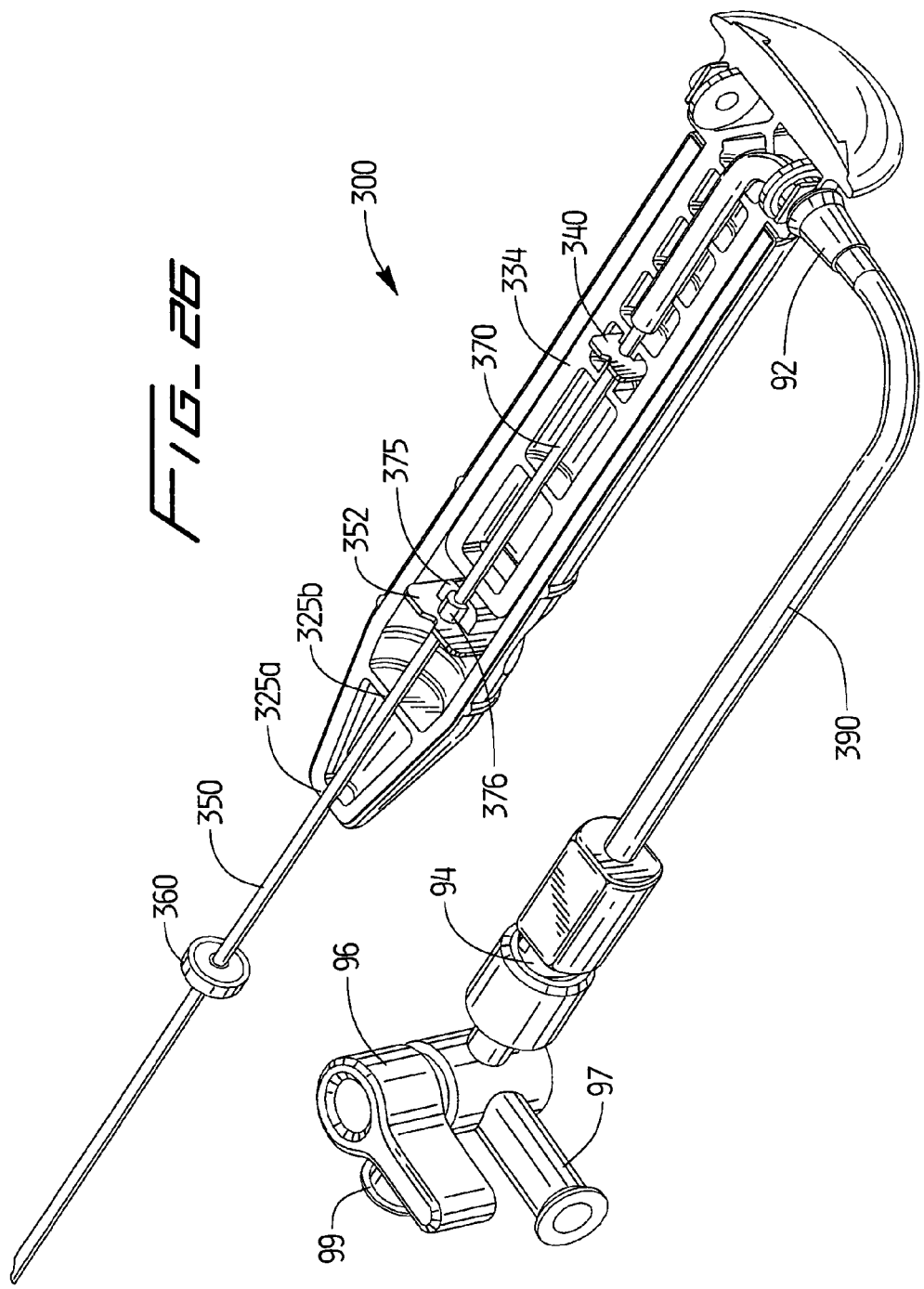

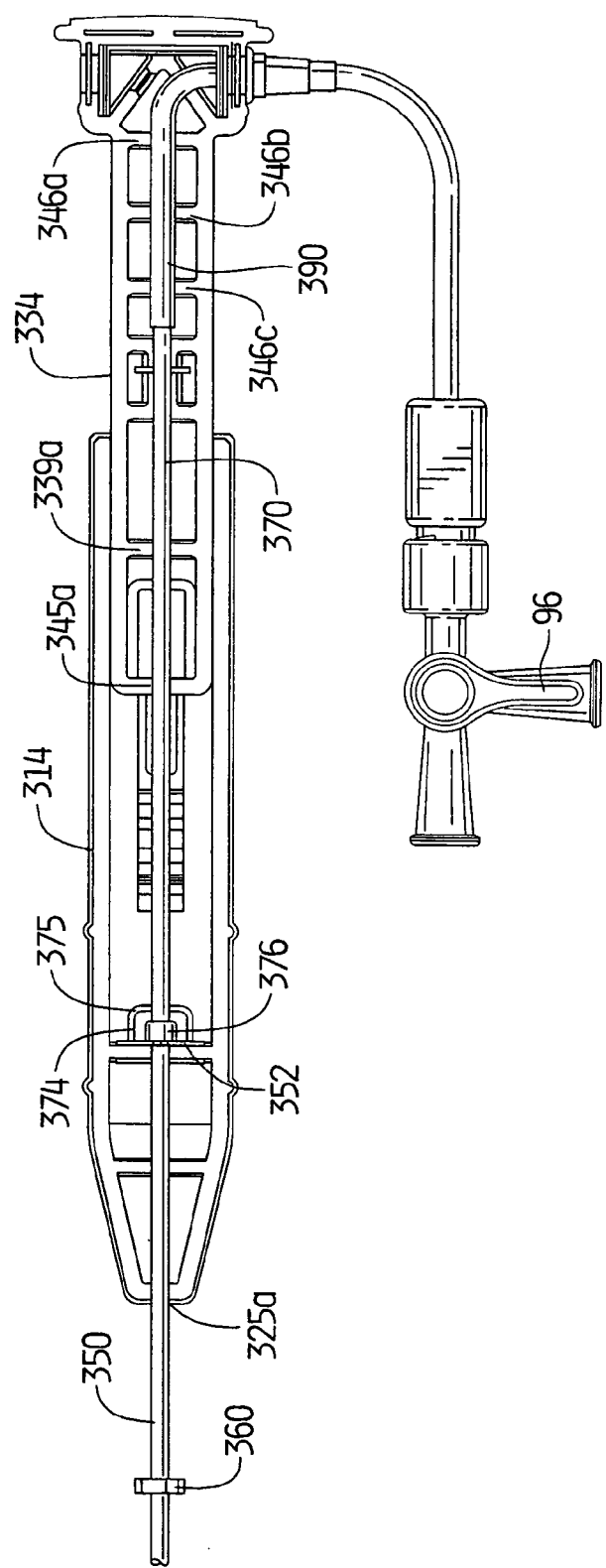

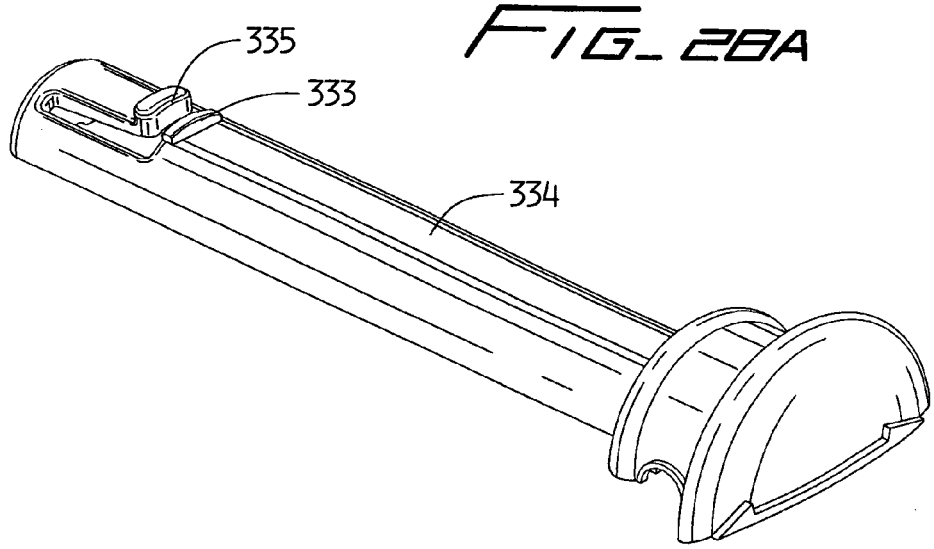
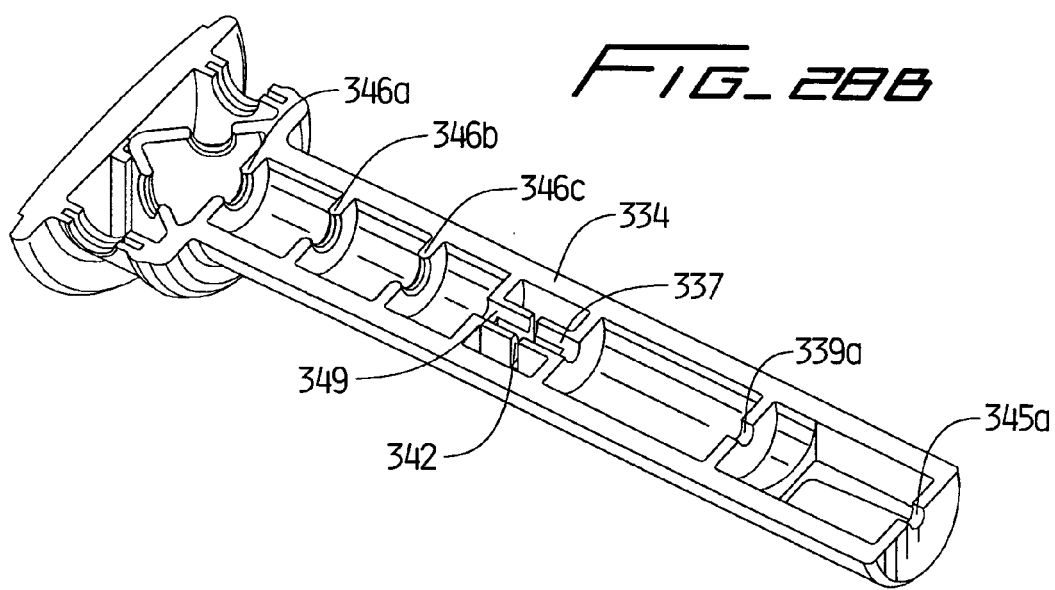

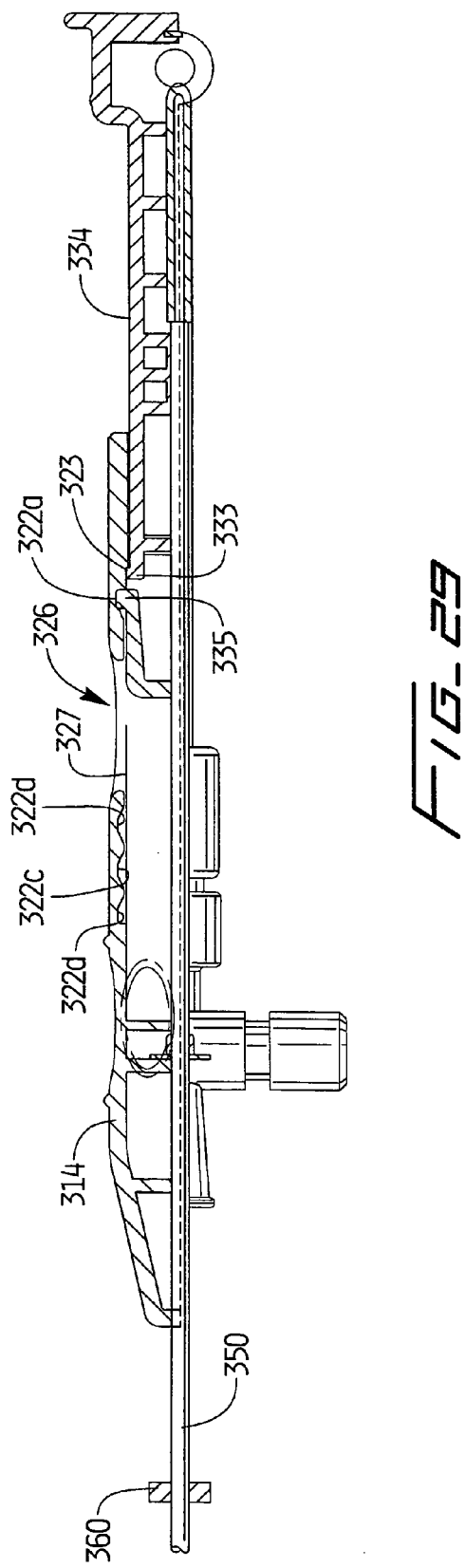

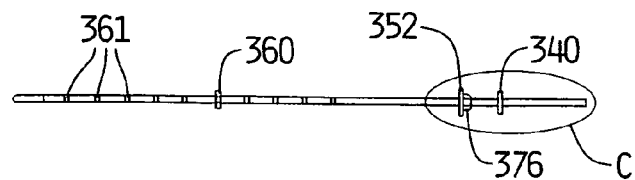
FIG_30
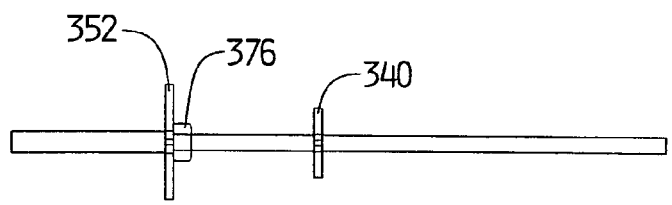
FIG_31
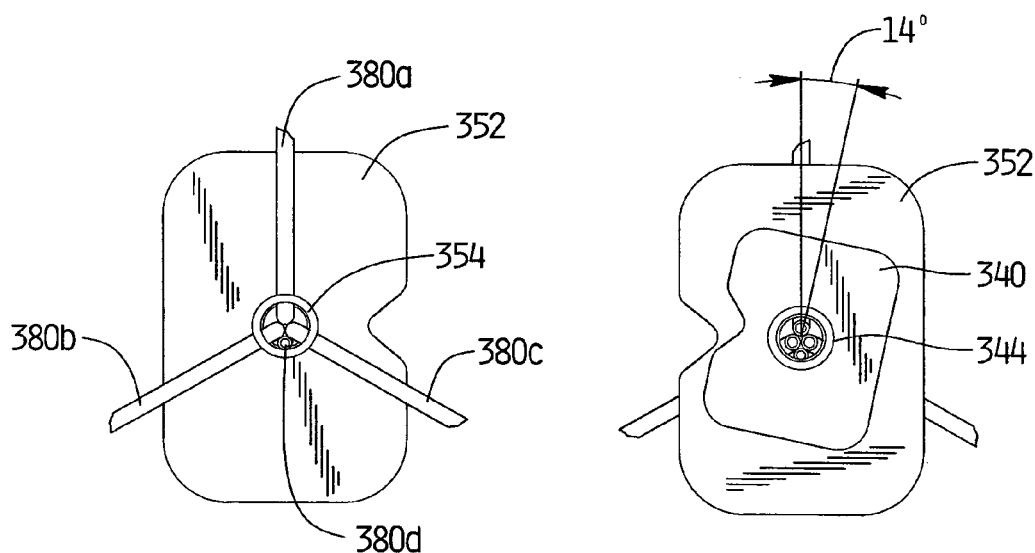
FIG_32A  FIG_32B

APPARATUS FOR DELIVERING ABLATION FLUID TO TREAT LESIONS

This application is a continuation of prior application Ser. No. 10/081,695 filed Feb. 22, 2002 now U.S. Pat. No. 6,905,480 which claims priority from provisional patent application Ser. No. 60/348,301 filed Nov. 7, 2001 and provisional patent application Ser. No. 60/272,119 filed Feb. 28, 2001. The entire contents of these applications are incorporated herein by reference.

BACKGROUND

1. Technical Field

This application relates to a surgical apparatus for treating lesions and more particularly to an apparatus that delivers ablation fluid such as acetic acid to ablate lesions.

2. Background of Related Art

One current method of treating hepatic (liver) cellular carcinomas is using electrosurgical energy in the form of radiofrequency energy. A series of electrodes are placed in the malignant tumor and a generator is activated to apply energy to the electrodes which heats the tissue to destroy the tumor. One example of such device is marketed by RITA Medical Systems which has an array of electrodes, offered in various configurations, which are curved outwardly from the tube in which they are constrained. It has been documented however in the literature that RF energy application is not consistently sufficient to ablate the cancerous tissue. Therefore, the patient must repeatedly return to the physician for additional applications of RF energy until the lesion is satisfactorily ablated. This not only adds to the expense of the procedure but can have an adverse psychological impact on the patient whose treatment is prolonged and characterized by frequent hospital visits. In additional to the clinical disadvantage, utilization of RF energy can be expensive since capital equipment, i.e. an RF generator for applying and controlling the electrosurgical energy, is required.

Another method of treating tumors is the injection of alcohol through a needle to ablate the tumor. The alcohol is typically about 95% to 99.5% ethanol and diffuses into the cancerous cells to produce immediate necrosis due to effects of cellular dehydration and protein denaturation followed by small vessel thrombosis.

One instrument currently being utilized to deliver ethanol to treat hepatic tumors is the Bernardino infusion needle, marketed by Cook of Bloomington, Ind. The needle is hollow and has two infusion ports adjacent the sharp distal tip. This device, however, has several disadvantages. The ethanol is injected only adjacent the distal tip, creating a relatively small treatment (ablation) zone. Therefore the needle must be repeatedly maneuvered and repositioned in various regions of the tumor and ethanol repeatedly injected until the entire tissue region has been treated. In fact, oftentimes the needle will have to be fully removed and reinserted into the patient, sometimes as frequently as twenty times in a single surgical procedure requiring twenty needle sticks, to ensure the entire region receives an adequate supply of ethanol.

Another method of treating tumors is the injection of acetic acid. The acetic acid has the additional advantage of penetrating the tumor septi and therefore providing more uniform chemical treatment of the lesion.

Commonly assigned co-pending provisional application Ser. No. 60/272,119, filed Feb. 28, 2001, the entire contents of which are incorporated herein by reference, discloses an instrument for delivering ethanol, acetic acid, or other ablation fluid which advantageously avoided the aforedescribed multiple needle sticks and limited ablation zone. The instrument disclosed in the '119 application provides a larger treatment zone to ablate a larger tumor, avoids multiple needle sticks, reduces the time required for treatment, and simplifies the surgical procedure. Additionally, it provides a more uniform treatment zone as well as the ability to vary the treatment zone so that the same delivery needle could be adapted for different sized lesions.

However, although the needle of the '119 application is effective, there is still a need to improve the zone of ablation by providing greater certainty of the location of the ablation needles and the boundary of the ablation zone. The instrument of the present application achieves these objectives in addition to providing the larger and more uniform needle treatment zone, the avoidance of multiple needle sticks, the ability to vary the treatment zone and simplification of the procedure as in the needle of the '119 application.

SUMMARY

The present invention advantageously provides a surgical apparatus for delivering fluid to treat a lesion comprising an elongated member having a distal tip and a plurality of openings formed in a sidewall proximal of the distal tip, a plurality of fluid delivery members movably positioned in the elongated member and having a lumen and at least one opening communicating with the lumen for delivering fluid to the lesion, and an actuator operatively associated with the fluid delivery members. The actuator is actuable to a first position to move the plurality of fluid delivery members from a retracted position within the elongated member to a first deployed position extending radially with respect to the elongated member and actuable to a second position to move the plurality of fluid delivery members from the first deployed position to a second deployed position extending further radially from the elongated member. The fluid delivery members are retained in the first and second deployed positions by a retention member.

Preferably the distal tip of the elongated member and the fluid delivery members are sharp to penetrate tissue. The actuator is preferably axially slidable to move the fluid delivery members between the retracted, first deployed and second deployed position, wherein in the deployed positions, a distal tip of the fluid delivery members does not extend distally of the distal tip of the elongated member. In a preferred embodiment, one of the fluid delivery members is extendable to a deployed position in substantial alignment with a longitudinal axis of the elongated member and has a diameter less than a diameter of the other fluid delivery members. The fluid delivery members can be composed of shape memory metal, or alternately of stainless steel.

The retention member preferably comprises a tab mounted on the actuator that engages one of the recesses formed in a housing through which the actuator is slidably received. A visible indicator may be provided to indicate the position of the plurality of fluid delivery members.

The present invention also provides a surgical apparatus for delivering fluid for tumor ablation comprising an elongated member having a lumen and a plurality of openings spaced proximally of a distalmost end of the elongated member, and first, second and third fluid delivery members movably positioned in the lumen of the elongated member. Each of the first and second fluid delivery members has a lumen and at least one opening in a sidewall communicating with the lumen of the fluid delivery member for delivering fluid to the lesion. The first and second fluid delivery members are movable between a retracted position, a first deployed position and a second deployed position, wherein the first and second fluid delivery members are substantially aligned with a longitudinal axis of the elongated member in the retracted position and extend through the respective openings in the elongated member at an angle to the longitudinal axis of the elongated member in the first and second deployed positions. The third fluid delivery member is substantially aligned with a longitudinal axis of the elongated member in a retracted position and in the deployed position.

Preferably, the third fluid delivery member has an outer diameter smaller than an outer diameter of the first and second fluid delivery members. An elongated guide may be mounted within the elongated member wherein the third fluid delivery member is slidable within the lumen of the guide. The third fluid delivery member is preferably proximal of the distalmost tip of the elongated member in the deployed position and the first and second fluid delivery members each have a distal tip, wherein the distal tip does not extend distally of the distalmost end of the elongated member. A plug can be positioned in the elongated member substantially flush with a distal edge of the elongated member to prevent coring of tissue as the elongated member is inserted.

The present invention also provides a surgical apparatus for delivering fluid to treat a lesion comprising a housing, an elongated member extending therefrom and having a distal tip and a plurality of openings in a sidewall, first and second fluid delivery members positioned in the elongated member and a visible indicator. The fluid delivery members each have a lumen and at least one opening in a sidewall communicating with the lumen for delivering fluid to the lesion. The first and second fluid delivery members are movable between a retracted position, a first deployed position and a second deployed position, wherein in the first and second deployed positions a distal tip of the fluid delivery members does not extend past a distal tip of the elongated member.

An actuator is operatively associated with the fluid delivery members and movable to move the first and second fluid delivery members from the retracted position to a first deployed position extending radially with respect to the elongated member and further movable to move the first and second fluid delivery members from the first deployed position to a second deployed position extending further radially with respect to the elongated member. In the deployed positions the first and second fluid delivery members extend through the respective openings in the sidewall of the elongated member. The visible indicator indicates the position of the first and second fluid delivery members.

The apparatus may also include a third fluid delivery member movable substantially longitudinally between a retracted position and a deployed position. The fluid delivery members can be composed of shape memory metal or stainless steel. The visible indicator preferably comprises an indicator visible through a window in the housing to indicate whether the fluid delivery members are deployed in the retracted, first or second deployed positions. The visible indicator can also comprise a marking at a proximal end of the apparatus to indicate the radial orientation of the members, wherein the marking is alignable with a skin-mounted patch through which the apparatus passes.

The present invention also provides a surgical apparatus for delivering fluid to treat a lesion comprising an elongated member having a distal tip, a plurality of openings formed in a sidewall proximal of the distal tip and a guiding structure extending inwardly from an inner surface of the elongated member. A plurality of fluid delivery members are movably positioned in the elongated member wherein each of the fluid delivery members has a lumen and at least one opening communicating with the lumen for delivering fluid to the lesion. An actuator is operatively associated with the fluid delivery members and is actuable to a first position to move the plurality of fluid delivery members from a retracted position within the elongated member to a first deployed position extending radially with respect to the elongated member and actuable to a second position to move the plurality of fluid delivery members from the first deployed position to a second deployed position extending further radially from the elongated member. The fluid delivery members are guided by the guiding structure through the respective opening in the sidewall of the elongated member. The guiding structure may comprise a protrusion formed integrally with the inner wall of the elongated member.

The present invention also provides a surgical apparatus for delivering fluid to treat a lesion comprising an elongated member having a sharpened distal tip, a plurality of openings formed in a sidewall proximal of the distal tip, and a cross-sectional circumference of between about 0.18 inches and about 0.22 inches. A plurality of hollow fluid delivery members are movably positioned in the elongated member, each of the fluid delivery members having a penetrating tip, a lumen, at least one opening communicating with the lumen for delivering fluid to the lesion and a cross-sectional circumference of between about 0.030 inches and about 0.040 inches. An actuator operatively associated with the fluid delivery members is actuable to a first position to move the plurality of fluid delivery members from a retracted position within the elongated member to a first deployed position extending radially with respect to the elongated member and actuable to a second position to move the plurality of fluid delivery members from the first deployed position to a second deployed position extending further radially from the elongated member.

A method for treating a lesion is also provided comprising:

inserting an apparatus adjacent the lesion;

advancing an actuator in a first direction to deploy a plurality of tines radially through side openings in the apparatus such that a distal tip of the tines does not extend distally of a distal tip of the apparatus; and injecting acetic acid through a lumen in the tines and through a plurality of side openings in the tines to ablate the lesion.

Preferably, the plurality of tines are composed of shape memory material and the method preferably further comprises the step of injecting saline through the tines prior to deployment, wherein the tines return to a shape memory configuration in response to warming by body temperature. In a preferred embodiment, the actuator advances a tine longitudinally to a substantially straight deployed positioned proximal of the distal tip of the apparatus.

BRIEF DESCRIPTION OF THE DRAWINGS

Preferred embodiment(s) of the present disclosure are described herein with reference to the drawings wherein:

FIG. 1 is a side view of the apparatus of the present invention in the initial position with the tines fully retracted within the needle;

FIG. 2 is a longitudinal sectional view of the apparatus of FIG. 1 showing the plunger in the initial position;

FIG. 2A is an enlarged cross-sectional view of the locking plate and seal;

FIG. 3 is a plan view of the apparatus of FIG. 1 with the second housing half and second plunger half removed showing the plunger in the initial position;

FIG. 4 is a perspective view showing the outer surface of the first plunger half;

FIG. 5 is a perspective view of the plunger half of FIG. 4, rotated 180 degrees to shown the inner region;

FIG. 6A is a perspective view of a region of the first housing half for mounting the inner tube;

FIG. 6B is a perspective view of a region of the first housing half illustrating the inner tube mounted therein;

FIG. 7A is a longitudinal sectional view of a portion of the apparatus of FIG. 1 at the region "A" showing the relationship of the tine guide and the inner tube;

FIG. 7B is a longitudinal sectional view of a portion of the apparatus proximal of the portion shown in FIG. 7A, (region "B" of FIG. 1), illustrating the shelf on the inner tube for engaging the tines;

FIG. 8 is a longitudinal cross-sectional view of the distal end portion of the apparatus of FIG. 1 in the initial position;

FIG. 9 is a perspective view of the needle plug;

FIG. 10 is a longitudinal sectional view showing a distal section of the apparatus (adjacent the needle openings) when the tines are in the initial retracted position;

FIG. 11 is a front view of the tines in the retracted position, with the tine guide and needle plug removed for clarity;

FIG. 12 is a side view of a portion of the apparatus of FIG. 1 when the tines are in the first deployed position;

FIG. 13 is a longitudinal sectional view of a portion of the apparatus showing the plunger in the first advanced position to advance the tines to the first deployed position;

FIG. 14A is a perspective view of a distal region of the apparatus illustrating the tines in the first deployed position;

FIG. 14B is an enlarged longitudinal sectional view illustrating the tines exiting through the side openings in the needle;

FIG. 14C illustrates the zone of tissue ablation for the first deployed tine position;

FIG. 15 is a front view of the tines in the first deployed position;

FIG. 16 is a side view of a portion of the apparatus of FIG. 1 when the tines are in the second deployed position;

FIG. 17 is a longitudinal sectional view of a portion of the apparatus showing the plunger in the second advanced position to advance the tines to the second deployed position;

FIG. 18 is a perspective view of a distal region of the apparatus illustrating the tines in the second deployed position;

FIG. 19 is a side view of the proximal portion of the apparatus of FIG. 1 when the tines are in the third deployed position;

FIG. 20 is a longitudinal sectional view of a portion of the apparatus showing the plunger in the third advanced position to advance the tines to the third deployed position;

FIG. 21 is a perspective view of a distal region of the apparatus illustrating the tines in the third deployed position;

FIG. 22 is a longitudinal sectional view of a distal region of the apparatus showing the tines in the third deployed position;

FIG. 23 is a perspective view of a portion of an alternate embodiment of the apparatus showing tabs to guide the tines through the windows;

FIG. 24 a perspective view of a portion of another alternate embodiment of the apparatus showing tabs to guide the tines through the windows;

FIG. 25 is a perspective view of another alternate embodiment of the apparatus having an orientation arrow at a proximal end to align with orientation markers on a skin patch;

FIG. 26 is a perspective view of another alternate embodiment of the apparatus of the present invention with the second housing half and second plunger half removed showing the plunger in the advanced position;

FIG. 27 is a plan view of the apparatus of FIG. 1 showing the first plunger half in the initial (retracted) position;

FIG. 28A is a perspective view of the first plunger half showing the tabs on the outer surface;

FIG. 28B is a perspective view of the plunger half of FIG. 28A, rotated 180 degrees to shown the inner region;

FIG. 29 is a longitudinal sectional view of the apparatus of FIG. 26 showing the plunger in the initial position;

FIG. 30 is a side view of the apparatus showing the tube retention and needle retention plates;

FIG. 31 in an enlarged view of the region "C" identified in FIG. 30;

FIG. 32A is a front view of the needle retention plate; and

FIG. 32B is a rear view of the needle retention and tube retention plates, prior to rotation of the tube rotation plate.

DETAILED DESCRIPTION OF PREFERRED EMBODIMENTS

Referring now in detail to the drawings where like reference numerals identify similar or like components throughout the several views, the apparatus of the present invention for delivering fluid for tumor ablation is designated generally by reference numeral 10 and illustrated in FIG. 1. Apparatus 10 includes a housing or body 12, an actuator or plunger 30, and an elongated tubular member or needle 50 extending distally from the housing 12. Positioned within the needle 50 are a plurality of fluid delivery tines which are movable with respect to the needle 50 in response to movement of the plunger 30. The tines contain openings for delivery of acetic acid or other ablation fluid to the target tissue and extend through respective side windows 52 in the needle 50 to a position proximal of the distal tip of the needle 50, thereby controlling the zone of acetic acid delivery and thus the zone of tissue ablation. Since the tines in FIG. 1 are in the retracted position within the needle 50, they are not visible in this Figure. FIGS. 14A, 18 and 21 show various deployed positions of the tines 80.

More specifically, and with reference to FIGS. 1-3, the housing 12 is composed of two identical housing halves 14 and 16. Proximal opening 28 of housing 12 slidably receives plunger 30 and distal opening 25 is configured to allow passage of the needle 50 therethrough. Since the housing halves are identical, for convenience, where applicable only one of the housing halves will be described and illustrated, it being understood that the other housing half would have the same structure and configuration. Note the terms "first" and "second" as used herein to describe the housing halves and plunger halves are solely for the purpose of clarity and convenience.

First housing half 14 includes finger recesses 17 to facilitate gripping by the surgeon in a tweezer-like fashion. A pair of rings 19a, 19b on either side of the recesses 17 also facilitate gripping of the apparatus. A plurality of recesses 22a, 22b, 22c and 22d are formed on an inner surface of first housing half 14 and are configured to receive a plunger tab 35 described below. Housing half 14 also has a cutout or window 26 which forms part of the visible indicator, also described below. As noted above, second housing half 16 is identical to first housing half 14 and is therefore not separately illustrated or described. It similarly contains recesses to receive a plunger tab and an indicator window.

Plunger (actuator) 30 is composed of identical plunger halves 34, 36, and therefore where applicable only one of the plunger halves will be described and illustrated in detail. First plunger half 34 has a flexible retention tab 35 (FIGS. 2 and 4), in the form of a detent, extending from an outer surface 33 and is positionable in one of the recesses 22a-22d of housing half 14, depending on the position of the tines with respect to the needle 50. An indicator 38 is formed on first plunger half 34 for visualization through window 26 of first housing half 14. In a preferred embodiment, the indicator is in the form of a pad printed dot that can be viewed through window 26 to indicate the position of the plunger 30 which in turn indicates the position of the tines 80 with respect to the elongated member 50. Other types of visual indicators are also contemplated such as other markings or projections protruding into window 26. Similarly, second plunger half 36 has a flexible retention tab to engage respective recesses on second housing half 16 and an indicator visible through a window in the housing half 16.

Plunger 30 is shown in the initial position in FIGS. 1-3 which corresponds to the proximalmost position of the tines in which they are retracted within needle 50. In this position, plunger tab 35 of plunger half 34 is in the first recess 22a of housing half 14. (Likewise, the plunger tab of the second plunger half 36 is in a first recess of second housing half 16) Also, in this position, indicator dot 38 on plunger half 14 is not visible in window 26 of housing 14 as it is positioned proximally of the window. When not visible, this indicates to the user that the tines 80 are fully retracted within the housing 12. Likewise, in this position, the indicator dot on the second plunger half 36 would also not be visible through the window in second housing half 16.

Housing half 14 and plunger half 34 have several mounting ribs and pockets which cooperate with identical ribs and pockets on housing half 16 and plunger half 36 to frictionally engage and retain inner support tube 70, plastic tubing 90 and needle 50. More specifically, and with reference to FIGS. 3, 5 and 6, tubing 90 is seated within cooperating ribs 46a, 48a, 46b, 48b and 46c, 48c of plunger halves 34 and 36, respectively. Tubing 90 has a lumen formed therein to accommodate fluid flow. Tubing 90 terminates at a distal end proximal of pocket 40 where it is frictionally fit over inner tube 70 to provide fluid communication between the lumen of tubing 90 and the lumen of inner tube 70. As shown in FIG. 3, tubing 90 is attached at a proximal end to luer fitting 94. Strain relief 92 is frictionally retained over tubing 90 to limit kinking of the tubing.

Distal round pockets 40a, 42a and elongated squared pocket 43a formed therebetween in plunger half 34 cooperate with corresponding round pockets 40b, 42b and square pocket on plunger half 36 to mount support (inner) tube 70. Inner tube 70 both transports fluid to the lumens of the tines 80 as well as moves the tines 80 between their retracted and deployed positions.

Inner tube 70 is preferably composed of metal and has a flattened (swaged) region received in pocket 43 to help prevent rotation of the inner tube 70. Inner tube 70 has a lumen extending therethrough and is connected at its proximal end to tube 90, preferably by a friction fit, to provide fluid communication with the lumen of the tube 90. The tines (fluid delivery members) 80 are attached to the distal end of inner tube 70, preferably by crimping or potting, so that axial movement of the inner tube 70 moves the tines axially. Glue or solder may further be used at the attachment to seal the connection to the tines 80 to prevent fluid leakage. The swaged region 72 of the inner tube 70 (shown in FIG. 7B), forms a shelf 74 for the tines 80. Inner tube 70 is in fluid communication with the lumens in the tines to deliver ablation fluid. Thus, flexible plastic tubing 90 (FIG. 3) communicates with support tube 70 to deliver fluid to support tube 70 which in turn delivers fluid to the tines 80. Plunger half 36, as noted above is identical to plunger half 34 so it also has the identical pockets and ribs cooperating with the pockets and ribs (e.g. pocket 40 and ribs 48 of FIG. 3) of plunger half 34 for receiving the inner tube 70 and plastic tubing 90.

Lock plate 79, as shown in FIGS. 2 and 3, is affixed to inner tube 70, preferably by welding or soldering, and is also affixed to inner wall 29a of the housing. Needle 50 extends through a central opening in plate 79. Press fit between the lock plate 79 and wall 29b is a seal 76 in the form of block frictionally seated over inner tube 70. Seal 76 prevents leakage of fluid proximally between the inner tube 70 and needle 50.

Needle (elongated member) 50 is seated within ribs 44a and groove 45a of plunger half 34 and cooperating ribs and groove 44b, 45b, respectively, on plunger half 36, and extends outwardly from the housing 12 through opening 25 a sufficient distance distally of housing 12 to enable access to the surgical site Needle 50 has a lumen dimensioned and configured to receive inner tube 70 and tines 80 for slidable movement therein.

Referring to FIGS. 1 and 3, the elongated member or needle 50 has a distal end 55 and a proximal end 54 extending into housing 12 and seated in ribs 44, 45 as described above. The distalmost tip of needle 50 is designated by reference numeral 56 and the outermost boundary of the needle 50 is demarcated by imaginary line L, the relevance of which is discussed below. The distalmost tip 56 of needle 50 is preferably sharp to penetrate tissue, preferably formed by a bevel. Needle 50 preferably has three windows 52, each dimensioned to provide an exit opening for one of the curved tines 80a-80c (discussed below). In one embodiment the windows 52 are spaced apart about 114 degrees, while the curved tines are spaced apart about 120 degrees. This positioning of the windows 26 and curved tines 80a, 80b and 80c accommodates the straight tine 80d. Other configurations and window/tine spacings are also contemplated.

Positioned within the distal portion of needle 50 is a needle plug 60 that fills the internal space of the distal end of the needle 50 to prevent coring of tissue when the apparatus is inserted. As best shown in FIGS. 8-10, needle plug 60 has an enlarged cylindrical plug portion 64 having a lumen 65 extending therethrough terminating in an axial opening 66. Positioned within the lumen 65, and extending proximally therefrom is stationary tine guide 68 having a lumen 69. Tine guide 68 is preferably flexible, is bent at region 71, as shown, and is configured to receive through its lumen one of the tines, namely straight tine 80d described below.

Turning now to the tines (fluid delivery members) of apparatus 10, in a preferred embodiment four tines are provided: three curved tines 80a, 80b and 80c and a straight tine 80d (see e.g. FIGS. 11 and 14A). The curved tines 80a-80c are configured to extend radially with respect to the longitudinal axis of the needle 50 when deployed and the straight tine 80d is designed to extend substantially parallel with respect to the longitudinal axis of the needle 50 when deployed. Each of the curved tines 80a-80c has a lumen, a plurality of openings 83a-83c in the side wall in fluid communication with the lumen, and a distal tip 85a-85c for penetrating tissue. The straight tine 80d has an axial opening at is distal end for delivering fluid through the distal end of the tine. Preferably, each of the curved tines 80a-80c has four side openings 83 communicating with the tine lumen for delivering fluid, e.g. acetic acid, to the tissue. In a preferred embodiment, the openings are about 90 degrees apart, with two of the openings which are opposite one another spaced slightly distally of the other two openings which are also opposite one another. Note that although four openings are provided in each curved tine 80a-80c, it is contemplated that fewer or more side openings can be provided on various portions of one or more of the tines to communicate with the lumen to achieve the desired effect.

With reference to FIGS. 10 and 11, in the initial position, tines 80a, 80b, and 80c are positioned proximal of their respective sidewall openings 52 formed in needle 50 and are substantially parallel with the longitudinal axis of the needle 50. In this initial position, straight tine 80d is positioned at a proximal portion of tine guide 68, also substantially parallel with the longitudinal axis of the needle 50.

Curved tines 80a, 80b 80c can be composed of shape memory material, such as a nickel titanium alloy, and when in the retracted position are in a substantially straightened position within the needle 50. When the tines are deployed, the curved tines 80a-80c extend through respective side openings 52 formed in the sidewall of needle 50 to assume a curved configuration such as that shown in FIG. 14a. The tines 80a-80c can be extended to various distances from needle 50 and retained at such distances by the interaction of plunger tab and housing recess as will be discussed below. The straight tine 80d remains in a substantially straight position within the needle 50 when deployed and is advanced through tine guide 68 a distance corresponding to the distance between recesses 22a and 22b. In a preferred embodiment, straight tine 80d has a diameter smaller than the diameter of the curved tines 80a-80c. This enables a reduction in the overall diameter of needle 50. It also enables a smaller volume of ablation fluid to be delivered to the surgical site through straight tine 80d. In a preferred embodiment, the straight tine 80d delivers a fluid volume one third the fluid volume of each of the curved tines 80a-80c. For example, the curved tines 80a-80c can each deliver a fluid volume of about 3 cc per minute, and the straight tine 80d can deliver a fluid volume of about 1 cc per minute. Other volumes are also contemplated.

It is also contemplated, as an alternative, to minimize space the straight tine can be of a very small size in the retracted position and the distal end of the tine, when it is advanced past the region where the curved tines exit through the needle openings, expands to a larger size.

Although various dimensions are contemplated, to minimize the size of the apparatus, the dimensions set forth below can be utilized. That is, minimizing the apparatus size, while maintaining adequate fluid supply and structural integrity in a 15-gauge needle can be achieved as follows by way of example. The straight tine 80d has an outer diameter of about 0.014 inches and an inner diameter of about 0.0085 inches and the curved tines 80a-80c each have an outer diameter of about 0.021 inches and an inner diameter of about 0.015 inches. The needle 50 outer diameter is about 0.070 inches and the inner diameter is about 0.058 inches. The curved tines each have four side holes 83 of 0.010 inches. This maximizes the openings without adversely affecting the structural integrity of the tine. The present apparatus is not limited to such dimensions as other dimensions are also contemplated.

In striking a balance between minimizing incision size and structural integrity, it has been found that the hollow tines could preferably have a diameter of between 0.010 inches and about 0.013 inches. In consideration of other cross-sectional configurations in addition to circular being utilized, then this threshold can also be considered in terms of circumference, and the circumference could be in the range of about 0.030 inches to about 0.040 inches. These dimensions can be utilized in an apparatus (needle) having an outer diameter of between about 0.058 inches and 0.072 inches, or stated another way, a circumference of between about 0.18 inches and 0.23 inches, and preferably about 0.22 inches. These dimensions will minimize the size of the overall needle incision while maintaining structural integrity of the tines and avoiding inadequate flow or excessive fluid pressure.

Note that to facilitate passage of the shape memory tines 80a-80c through needle 50 and into the tissue, cold saline is injected through the tines 80a-80c in their retracted position within needle 50. Tines 80a-80c are composed of shape memory metal, such as Nitinol, a nickel titanium alloy, which characteristically exhibits rigidity in the austenitic state and more flexibility in the martensitic state. The cold saline maintains the temperature dependent tines 80a-80c in a relatively softer condition as they are in a martensitic state within needle 50. This facilitates their exit from needle 50 as frictional contact between the tips 85a-85c of the tines 80a-80c and the inner wall of the needle 50 would otherwise occur if the tines were maintained in a rigid condition. After deployment, i.e. advancement from needle 50, the tines 80a-80c are exposed to the warmer body, temperature. This change in temperature causes the tines 80a-80c to achieve their desired degree of rigidity as they transition to their austenitic state to facilitate passage through the tissue. Their warming thus enables them to return to their memorized configuration at an angle to the longitudinal axis of needle 50. Tine 80d can also be composed of shape memory material and can be infused with saline. Note that in an alternate embodiment, stainless steel curved and/or straight tines can be utilized. The stainless steel curved tines would move to a curved position when deployed.

FIGS. 23 and 24 show alternate configurations to help orient the curved tines 80a-80d to direct them out the windows in the needle. In FIGS. 23 and 24, multiple protrusions are formed on the inner surface of the needle 250, 250 adjacent the windows 252, 252' respectively. This can be achieved for example by laser cutting slots 220 as in FIG. 23 to form tabs 254 or dimples or indentations 230 as in FIG. 24 by denting the wall of the needle 250'. Four protrusions or indentations are preferably provided and are preferably spaced about 90 degrees apart so the tip of the tine will slide between two adjacent protrusions/indentations, thereby keeping it aligned as it advances through the respective window.

FIGS. 12-15 illustrate a first deployed position of the tines 80a-80d. To achieve this position, plunger 30 is advanced distally in the direction of the arrow until plunger tab 35 is engaged in recess 22b of housing half 14 (as well as the plunger tab of plunger half 36 engaged in the second recess of housing half 16) to retain the plunger 30 in that position as well as provide a tactile feel to the user that the tines 80a-80d have been deployed to their initial position.

As plunger 30 is slid axially in a distal direction towards the housing 12, inner tube 70 is advanced axially to advance curved tines 80a-80c through the respective side openings 52 of needle 50, enabling the tines 80a-80c to extend angularly with respect to the longitudinal axis "a" of the needle 50 as shown. Axial sliding of plunger 30 also advances straight tine 80d distally, through guide 68.

In this first deployed position, indicator dot 38 of first plunger half 14 appears at the proximal portion of the window 26, providing a visual indication to the user that the tines 80a-80c have been deployed to their first position. Likewise the indicator dot of plunger half 36 appears in the respective window of housing half 16.

FIGS. 16-18 illustrate the tines 80a-80c in a second deployed position. In this position, the plunger 30 has been slid further distally towards the housing 12, a greater distance than in FIG. 12. Plunger tab 35 of plunger half 34 is engaged with the third recess 22c in housing half 14 and the plunger tab of second plunger half 36 is likewise engaged in the third recess of housing half 16. This deploys the tines 80a-80c further radially from the longitudinal axis of the needle 30, such that their distal tips are a greater distance from the longitudinal axis "a" of the needle 50, providing a larger tissue treatment zone. Straight tine 80d advances a distance corresponding to the distance between recesses 22b and 22c. As shown in FIG. 16, indicator dot 38 has advanced to a middle portion of the window 26 to indicate the tines 80 have been deployed to a second deployed position. (The indicator dot on second plunger half is likewise moved.)

FIGS. 19-22 illustrate the tines 80a-80c in a third deployed position. In this position, the plunger has been slid further distally towards the housing 12 a greater distance than in FIG. 16 and plunger tab 35 is received in fourth recess 22d. Likewise the plunger tab of second plunger half 36 is received in the fourth recess of housing half 16. This deploys the tines 80a-80c further radially from the longitudinal axis of the needle 30, such that their distal tips are an even greater distance from the longitudinal axis of the needle 50, thereby providing an even larger tissue treatment zone. Straight tine 80d advances a distance corresponding to the distance between recesses 22c and 22d. As shown in FIG. 19, indicator dot 38 has advanced to a distal portion of the window to indicate the tines 80 have been deployed to a third deployed position. (The indicator dot on the second plunger half is likewise moved into respective position in the window of second housing half.)

As illustrated, curved tines 80a-80c and straight tine 80d remain proximal of distal tip in the deployed positions. This better controls the zone of tissue ablation. This is a result of the fact that in use the distal tip of the needle 50 is typically placed at the distal end of the lesion. Therefore, when the tines 80a-80c are deployed, the surgeon can be assured that the tines remain proximal of the distal edge of the lesion, thereby better controlling injection of ablation fluid inside the lesion.

In use, the apparatus 10 is inserted percutaneously through the skin to the target tissue site with the beveled edge 56 of needle 50 forming a cutting edge to penetrate tissue to facilitate passage of apparatus 10 to the surgical site. Needle plug 60 prevents coring of the tissue during insertion of apparatus 10. The apparatus 10 is inserted with plunger 30 in the initial or neutral position so that tines 80a-80d are fully retracted inside needle 50 as shown in FIG. 1. Saline is delivered through the shape memory tines 80. If a smaller treatment zone is desired, e.g. 3 cm, plunger 30 is pushed axially inwardly, with the plunger retention tabs disengaging from the respective first recesses, e.g. recess 22a, and advanced into respective second recesses, e.g. recess 22b, of each housing half of housing 12. This deploys the tines 80a-80c to the position of FIG. 14a with the tips 85a, 85b and 85c penetrating tissue and tine 80d moving axially towards the distal tip 56 of apparatus 10. Note that indicator dot 38 has moved into window 26 as shown in FIG. 12, indicating to the user that the plunger 30 has been moved from its initial position.

Next, saline delivery is terminated and acetic acid (or other ablation fluid) is injected through a tube of a stopcock which is threadedly attached to luer fitting 94, flowing through tubing 90 and inner tube 70, and through the lumens in tines 80a-80d, exiting through holes 83a-83c in curved tines 80a-80c and through the axial opening in straight tine 80d. In this first deployed position, tine 80d remains in a straight position substantially aligned with the longitudinal axis of the needle 50, terminating proximal of distal tip 56, and the other three tines 80a, 80b and 80c extend outwardly at an angle to the longitudinal axis, as they return to their memorized configuration in response to exposure to warmer body temperature, to create a first treatment zone Z1. As shown in FIG. 14C, in this first deployed position, due to the deployed configuration of the tines and the placement of the fluid delivery openings, the portion of the lesion that is ablated by the ethanol is defined by the four intersecting spheres designated "Z1".

A three way stopcock such as that disclosed in FIG. 6A of the '119 application, incorporated herein by reference, can be provided to enable acetic acid to be inserted through tube 90 when the stopcock is in a first position, allow cold saline to be inserted through tube 90 when stopcock 112 is in a second position (rotated 90 degrees with respect to the first position), and prevent fluid flow when the stopcock is in the third position.

To create a larger treatment zone, the plunger 30 is pushed further inwardly until retention tab 35 of plunger 34 is engaged with third recess 22c and the retention tab of plunger 36 is likewise engaged with the third recess of housing half 16. This deploys the tines to the position of FIG. 18 as they are advanced from the needle 50 and exposed to warmer body temperature to return to their memorized configuration as they transition from the martensitic to the austenitic state.

Note that indicator dot is in a central portion of window 26, indicating that the plunger 30 has been further advanced to move the tines 80 to the second deployed position. In this position, the tines 80a-80c extend at a greater angle with respect to the longitudinal axis of the needle 50 and a greater angle with respect to the straight tine 80d. Thus, when acetic acid is injected through the tines 80a-80d, four intersecting spherical areas are created which occupy a larger area than the spheres of FIG. 14C to create a larger treatment zone.

If an even larger treatment zone is desired, the plunger 30 is pushed even further inwardly until the retention tabs of the plunger halves 34, 36 are engaged with the fourth recesses, e.g. recess 22d, in the respective housing halves 14, 16. This deploys the tines to the position of FIG. 21 as they are advanced from the needle 50

If creation of an even larger treatment zone or filling in the zone between the four spherical areas is desired, the user injects saline to cool the tines 80, retracts the tines into needle 50, and then rotates the entire apparatus, or otherwise repositions the apparatus 10, and redeploys the tines to inject acetic acid. To facilitate locating the needle if rotation is desired, a skin patch 200 as shown in FIG. 25 can be provided with alignment markings, spaced about 60 degrees apart, by way of example. The skin patch is preferably mounted to the skin by adhesive and has an opening to allow passage of the apparatus therethrough. The apparatus can include an orientation arrow 210 to provide a visual alignment indicator with the markings of skin patch 200. By orienting the arrow in alignment with the skin patch markings, the user can better control 60 degree rotational changes of the apparatus (or other variations dependent on the spacing of the markings) as the marking will indicate the radial orientation of the tines.

FIGS. 26-32 illustrate another alternate embodiment of the apparatus of the present invention for delivering ablation fluid. Apparatus 300 differs from apparatus 10 of FIG. 1 in the attachment of the inner support tube, the provision of an anti-twist tab on the plunger, the orientation of the tines with respect to the needle, and the provision of a depth marker. In all other respects, the apparatus 300 of FIGS. 26-32 is identical to, and functions in the same manner as apparatus 10 of FIG. 1.

More specifically, apparatus 300, like apparatus 10, has a housing or body 312 composed of two identical housing halves (only first housing half 314 is shown), an actuator or plunger 330 composed of two identical plunger halves (only first plunger half 334 is shown) and an elongated member (needle) 350 extending from housing 10. As shown in FIG. 29, a plurality of recesses 322a, 322b, 322c and 322d are formed on the inner surface of housing half 314 and configured to receive flexible retention tab 335 of first plunger half 314. Similar recesses are formed on housing half 316 to receive the retention tab of the second plunger half. The flexible retention tabs are respectively receivable in one of the recesses, depending on the position of the plunger 330 and tines 380 with respect to the needle 350, to thereby retain the plunger 330 and tines 380 in their respective position in the manner described above with respect to apparatus 10 of FIG. 1. Plunger half 334 also includes a rigid tab 333 extending from its outer surface to engage slot 323 in the housing half 314. This rigid tab rides along ledge 327 to prevent twisting of the plunger 330. An identical tab is formed on the second plunger half for engagement with a slot in the second housing half. An indicator, such as indicator 38 of FIG. 4, can be provided on each of the plunger halves to provide, through a window (e.g. window 326) on each housing half, a visual indication of the position of the tines 380.

First housing half 314 and first plunger half 334 have several mounting ribs and pockets which cooperate with identical ribs and pockets on the second housing half and second plunger half 336 to frictionally engage and retain inner support tube 370, retention plates 340, 352, plastic tubing 390 and needle 350. More specifically, and with reference to FIGS. 26, 27 and 28B, tubing 390 extends into plunger 330 and is seated within ribs 346a, 346b, and 346c of first plunger half 334 (and cooperating ribs of second plunger half 336). Tubing 390 terminates at a distal end proximal of slot 349 where it is frictionally fit over inner tube 370 to provide fluid communication between the lumen of tubing 390 and the lumen of inner tube 370. Tubing 390 is attached at a proximal end to luer fitting 94 and strain relief 92 is frictionally retained over tubing 390 to limit kinking of the tubing. A three way stopcock 96 is provided, functioning as described above and in the '119 application, to enable infusion of ablation fluid through a tube attached to fitting 97 or cold saline through a tube attached to fitting 99.

A tube retention plate 340 is seated within transverse recess 342 intersecting longitudinal pocket 337 of plunger half 334 (and likewise identically formed in the second plunger half). Inner tube 370 is seated within pocket 337 and extends through, in frictional engagement with, central opening 344 of tube plate 340. (see also FIG. 32). The tines (fluid delivery members) 380 are attached to the distal end of inner tube 370, preferably by crimping, potting, or gluing so that axial movement of the inner tube 370 moves the tines axially. Flexible plastic tubing 390 (FIG. 26) communicates with support tube 370 to deliver fluid to support tube 370 which in turn delivers fluid to the tines 380.

Needle 350 is seated within recesses 325b of housing half 314 and cooperating recess on the second housing half (not shown). Needle 350 is further mounted by a needle retention plate 352 seated within a recess in first housing half 314 (and identical recess formed in the second housing half 316). Needle 350 extends through opening 354 in needle plate 352 and through distal opening 325a of housing 314. A seal 376, seated within a pocket on block 375 and abutting plate 352, is fitted over tube 370 at the juncture with needle 350 to prevent leakage of fluids proximally between the inner tube 370 and needle 350.

Needle 350 includes a series of sidewall openings which form exit apertures for the curved fluid delivery tines 380a-380c. The tines 380a-380c are deployed to the positions corresponding to the aforedescribed positions of tines 80-80c of apparatus 10. A straight tine 380d (FIG. 32A) is also preferably provided in the same way as in the FIG. 1 embodiment. The curved tines 380a-380c have openings through the side walls as described above with respect to tines 80a-80c.

The tines 380-380c are preferably offset with respect to the exit apertures (windows) of needle 350 to facilitate passage therethrough. This offset alignment is best shown in FIGS. 32A-32B. Prior to assembly, the top tine as viewed in FIG. 32A is aligned with an axis parallel to a transverse axis of the needle retention plate 352. The tube retention plate 340 is assembled at an angle to the plate 352 as shown in FIG. 32B, and then rotated counterclockwise approximately 14 degrees to correspondingly rotate the tines 14 degrees to move the tines out of phase with respect to the exit apertures in needle 350 to facilitate passage therethrough. That is, the exit apertures in the needle 350 are preferably formed so that the two side apertures are approximately 106 degrees apart from the "top" aperture (using FIG. 32 as a reference) which accommodates tine 380a. Since the two tines 380b and 380c are preferably 120 degrees apart from tine 380a during assembly, this offset with respect to the apertures accommodates for the torquing motion of the tines to enable smooth passage through the side apertures in the needle 350. This is due to the fact that the tines in exiting will both bend and twist and follow the path of least resistance. As appreciated these angles are provided by way of example, as other angles besides 14 degrees, preferably ranging from between about 8 degrees to about 20 degrees out of phase, could also be provided. For stainless steel tines the angle is preferably between about 20 degrees and 30 degrees and preferably about 23 degrees. Also note that since the needle 350 needs to accommodate the small straight tine 380d and the tine guide, the tines may not be equidistantly spaced, as for example, tines 380b and 380c could be spaced approximately 145 degrees apart.

A marking ring 360 is mounted on needle 320 to provide a depth indicator for apparatus 300. A series of markings 361 (only a few are labeled in FIG. 30 for clarity) can be provided along the length of the needle 350 to indicate the depth of penetration, i.e. the distance from the distal tip of the needle 350 to the marking ring 360. Prior to insertion, the surgeon would slide the marking ring 360 along the needle length to align with the desired depth marking. This would define the extent of penetration since the surgeon would insert the apparatus 300 until resistance was felt by the marking ring 330 against the skin. Thus, the depth of penetration could be predetermined and better controlled. Note that the marking ring 360 could also be provided on the other embodiments of the apparatus described herein.

Additionally, apparatus 300 can be provided with orientation arrows to align with a skin patch as in FIG. 25 and/or the orientation structure of FIGS. 23 and 24.

It is contemplated that the apparatus of the present invention injects acetic acid into the tumor to ablate the tumor. The acetic acid diffuses into the cancerous cells, burning through the tumor septi, i.e. the compartments within the tumor, to produce immediate necrosis due to effects of cellular dehydration and protein denaturation followed by small vessel thrombosis. The volume of acetic acid and the number of infusions can vary. However, it is also contemplated that the apparatus of the present invention can be used to deliver other fluids such as hot saline or ethanol to ablate the tissue. Also, although contemplated for treating hepatic (liver) tumors, it is also contemplated that the apparatus can be utilized to treat tumors in other regions of the body such as the spleen, pancreas, or brain. The apparatus can also be used to inject other fluids, e.g. therapeutic fluids such as chemotherapeutic agents or gene cells.

While the above description contains many specifics, those specifics should not be construed as limitations on the scope of the disclosure, but merely as exemplifications of preferred embodiments thereof. For example, the flexible retention tab can be positioned on the housing and the series of recesses positioned on the plunger. Those skilled in the art will envision many other possible variations that are within the scope and spirit of the disclosure as defined by the claims appended hereto.

What is claimed is:

1. A surgical apparatus for delivering fluid to treat a lesion comprising:
   a housing;
   an elongated member extending from the housing and having a distal tip and a plurality of openings formed in a sidewall proximal of the distal tip, the openings having a first angular spacing with respect to a longitudinal axis of the elongated member;
   a plurality of hollow fluid delivery members movably positioned in the elongated member, each of the fluid delivery members having a penetrating tip, a lumen and at least one opening communicating with the lumen for delivering fluid to the lesion, the fluid delivery members having a second angular spacing different from the first angular spacing and extendable through the openings in the sidewall of the elongated member;
   a first tube retaining the fluid delivery members at a proximal end thereof and communicating with the fluid delivery members;
   a first retention member retaining the first tube, the retention member being rotated during assembly and fixed in the rotated position;
   a second retention member positioned in the housing, the second retention member retaining the elongated member in the housing; and
   an actuator operatively associated with the fluid delivery members, the actuator actuable to a first position to move the plurality of fluid delivery members from a retracted position within the elongated member to a first deployed position extending radially with respect to the elongated member and actuable to a second position to move the plurality of fluid delivery members from the first deployed position to a second deployed position extending further radially with respect to the elongated member;
   wherein the first retention member comprises a first plate having an opening therethrough to receive the first tube and the second retention member comprises a second plate having an opening therethrough to receive the elongated member.

2. The apparatus of claim 1, wherein the first and second plates are assembled at an angle to each other.

3. A surgical apparatus for delivering fluid to treat a lesion comprising:
   a housing having a longitudinal axis;
   an elongated member extending from the housing and having a distal tip and a plurality of openings formed in a sidewall proximal of the distal tip, the openings having a first angular spacing with respect to a longitudinal axis of the elongated member;
   a plurality of hollow fluid delivery members movably positioned in the elongated member, each of the fluid delivery members having a lumen and at least one opening communicating with the lumen for delivering fluid to the lesion, the tips of the fluid delivery members extendable through the openings in the sidewall of the elongated member;
   an actuator for moving the fluid delivery members;
   a first tube retaining the fluid delivery members at a proximal end thereof and communicating with the fluid delivery members;
   a first retention member configured to retain the first tube; and
   a second retention member spaced axially distally from the first retention member and positioned within the housing and configured to retain the elongated member, the second retention member being axially fixed within the housing.

4. The apparatus of claim 3, wherein the first and second retention members are assembled at an angle to each other so the fluid delivery members have an angular spacing different than an angular spacing of the openings in the sidewall of the elongated member.

5. The apparatus of claim 3, wherein the first retention member comprises a first plate having an opening therethrough to receive the first tube and the second retention member comprises a second plate having an opening therethrough to receive the elongated member.

6. The apparatus of claim 3, wherein the fluid delivery members are movable from a retracted position within the elongated member to a first deployed position extending radially with respect to the elongated member and further movable from the first deployed position to a second deployed position extending further radially from the elongated member, and the apparatus further comprises a third retention member, the retention member retaining the plurality of fluid delivery members in the first and second deployed positions.

7. The apparatus of claim 3, wherein the actuator further comprises a plunger, the plunger having a recess to receive the first retention member.

8. The apparatus of claim 3, further comprising a seal positioned within the housing to prevent leakage between the first tube and the elongated member.

9. A surgical apparatus for delivering fluid to treat a lesion comprising:
   a housing;
   an elongated member extending from the housing and having a distal tip and a plurality of openings formed in a sidewall proximal of the distal tip, the openings having a first angular spacing with respect to a longitudinal axis of the elongated member;
a plurality of hollow fluid delivery members movably positioned in the elongated member, each of the fluid delivery members having a lumen and at least one opening communicating with the lumen for delivering fluid to the lesion, the tips of the fluid delivery members extendable through the openings in the sidewall of the elongated member;
an actuator for moving the fluid delivery members;
a first tube retaining the fluid delivery members at a proximal end thereof and communicating with the fluid delivery members;
a first retention member configured to retain the first tube; and
a second retention member spaced axially distally from the first retention member and positioned within the housing and configured to retain the elongated member;
wherein the first and second retention members are assembled at an angle to each other so the fluid delivery members have an angular spacing different than an angular spacing of the openings in the sidewall of the elongated member.

10. The apparatus of claim 9, wherein the fluid delivery members are movable from a retracted position within the elongated member to a first deployed position extending radially with respect to the elongated member and further movable from the first deployed position to a second deployed position extending further radially from the elongated member, and the apparatus further comprises a third retention member, the retention member retaining the plurality of fluid delivery members in the first and second deployed positions.

11. The apparatus of claim 9, wherein the actuator further comprises a plunger, the plunger having a recess to receive the first retention member.

12. The apparatus of claim 9, further comprising a seal positioned within the housing to prevent leakage between the first tube and the elongated member.

* * * * *

Disclaimer 7,344,518—James F. McGuckin, Jr., Radnor, PA (US); Stephan A. DeFonzo, Wayne, PA (US); Alim S. Alli, North Haven, CT (US); Peter W. J. Hinchliffe, Downington, PA (US). APPARATUS FOR DELIVERING ABLATION FLUID TO TREAT LESIONS. Patent dated March 18, 2008. Disclaimer filed September 18, 2007, by the assignee, Rex Medical, L.P.

Hereby disclaims the terminal part of any patent granted on the above-identified application, which would extend beyond the expiration date of the full statutory term of U.S. Patent No. 6,905,480.

*(Official Gazette September 30, 2008)*